(12) United States Patent
Williamson

(10) Patent No.: US 7,273,500 B2
(45) Date of Patent: *Sep. 25, 2007

(54) INSTRUMENTS AND METHODS FOR USE IN PERFORMING KNEE SURGERY

(76) Inventor: Richard V. Williamson, 11472 "O" Ave., Anacortes, WA (US) 98221

( * ) Notice: Subject to any disclaimer, the term of this patent is extended or adjusted under 35 U.S.C. 154(b) by 36 days.

This patent is subject to a terminal disclaimer.

(21) Appl. No.: 10/974,071

(22) Filed: Oct. 26, 2004

(65) Prior Publication Data

US 2005/0085920 A1   Apr. 21, 2005

Related U.S. Application Data

(62) Division of application No. 10/151,811, filed on May 20, 2002, now Pat. No. 6,942,700, which is a division of application No. 09/575,691, filed on Jun. 29, 2000, now Pat. No. 6,478,799.

(51) Int. Cl.
*A61F 2/38*   (2006.01)
(52) U.S. Cl. .................................... 623/20.14
(58) Field of Classification Search ... 623/20.14–20.36
See application file for complete search history.

(56) References Cited

U.S. PATENT DOCUMENTS

| | | | |
|---|---|---|---|
| 4,524,766 A | 6/1985 | Petersen | 128/92 |
| 4,738,253 A | 4/1988 | Buechel et al. | 128/92 |
| 4,938,762 A | 7/1990 | Wehrli | 606/88 |
| 4,952,213 A | 8/1990 | Bowman et al. | 606/79 |
| 5,122,144 A | 6/1992 | Bert et al. | 606/88 |

(Continued)

FOREIGN PATENT DOCUMENTS

EP    0 714 645 A1    6/1996

(Continued)

OTHER PUBLICATIONS

"Zimmer Scandinavia" Presentation Materials, Joakim Rang, 2000.

*Primary Examiner*—Cary E. O'Connor
(74) *Attorney, Agent, or Firm*—Seed IP Law Group, PLLC

(57) ABSTRACT

A system and method for aligning a patient's leg, for establishing the ultimate alignment of the leg prior to making a horizontal femoral cut or a horizontal tibial cut, for preparing the distal femur for receiving a femoral implant, and for making the horizontal, femoral and tibial cuts. The system and method incorporate a spacer, a cutting guide, and a template. The spacer is insertable between a distal femur and a proximal tibia to rotate the tibia with respect to the femur into the desired alignment. The cutting guide is engageable with the spacer, and can be fixed to the proximal tibia and the distal femur. The cutting guide has openings sized and shaped to guide a surgical saw to make the horizontal femoral cut and the horizontal tibial cut. The template is shaped to closely conform with the distal femur to allow the leg to be extended and to allow the procedure to be performed without dislocating a patella. Through one method of the present invention, the practitioner can select the desired ultimate alignment of the leg prior to making the horizontal, tibial and femoral cuts. As a result, when a replacement knee is implanted, the leg will be in the desired alignment.

19 Claims, 17 Drawing Sheets

U.S. PATENT DOCUMENTS

| | | | |
|---|---|---|---|
| 5,213,112 A | 5/1993 | Niwa et al. | 128/774 |
| 5,234,433 A | 8/1993 | Bert et al. | 606/88 |
| 5,304,181 A | 4/1994 | Caspari et al. | 606/80 |
| 5,312,411 A | 5/1994 | Steele et al. | 606/88 |
| 5,464,406 A | 11/1995 | Ritter et al. | 606/86 |
| 5,540,696 A | 7/1996 | Booth, Jr. et al. | 606/88 |
| 5,597,379 A | 1/1997 | Haines et al. | 606/80 |
| 5,669,914 A | 9/1997 | Eckhoff | 606/88 |
| 5,735,904 A | 4/1998 | Pappas | 623/20 |
| 5,800,438 A | 9/1998 | Tuke et al. | 606/90 |
| 5,902,339 A | 5/1999 | Keller | 623/20 |
| 5,911,723 A | 6/1999 | Ashby et al. | 606/88 |
| 6,080,196 A | 6/2000 | Bertin | 623/20.14 |
| 6,174,314 B1 | 1/2001 | Waddell | 606/88 |

FOREIGN PATENT DOCUMENTS

| | | |
|---|---|---|
| EP | 0 809 969 A | 12/1997 |
| FR | 2 648 699 A | 12/1990 |
| WO | WO96/13233 | 5/1996 |
| WO | WO98/32384 | 7/1998 |

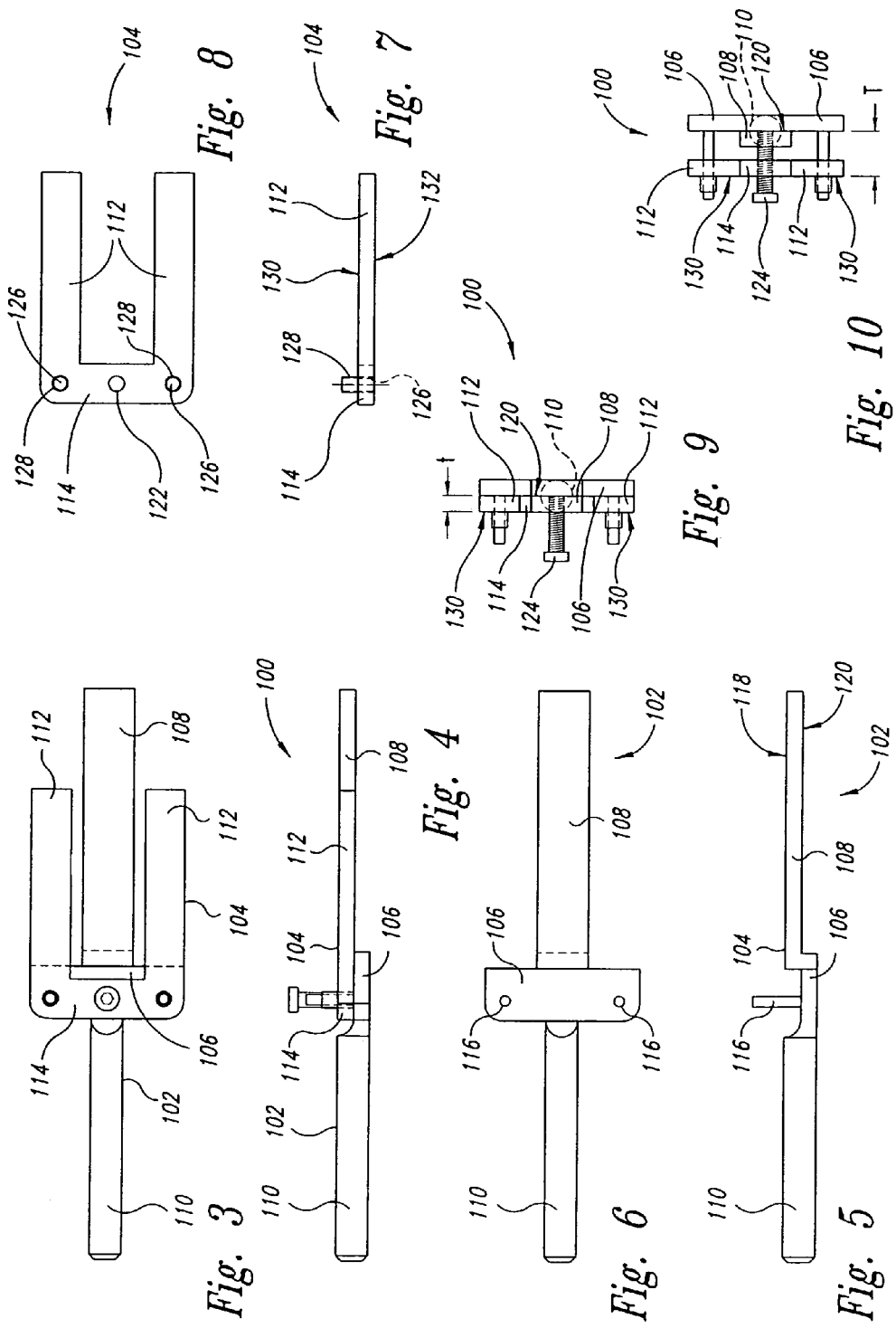

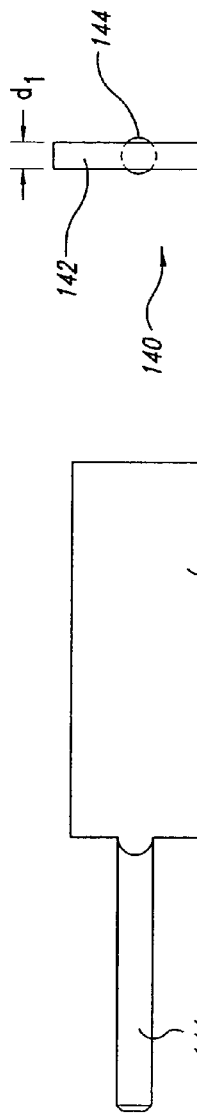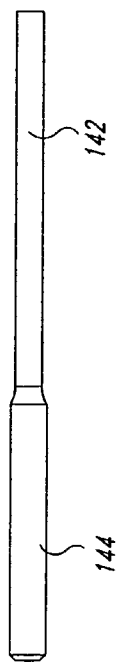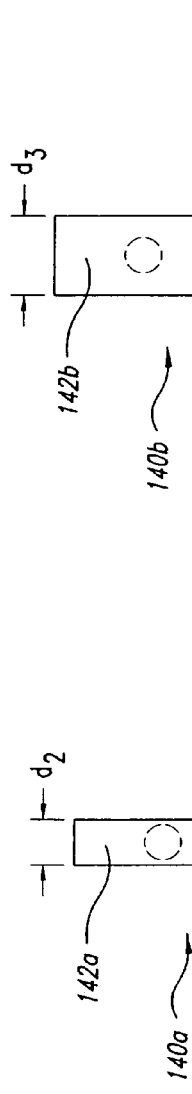

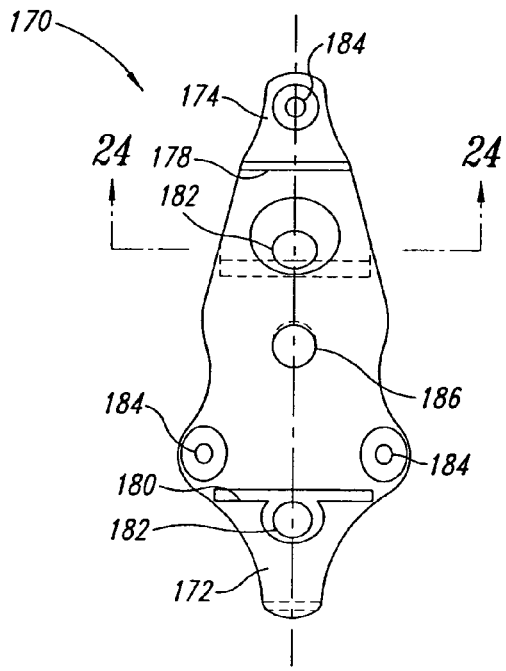
Fig. 21
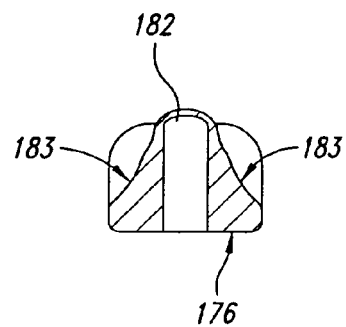
Fig. 24
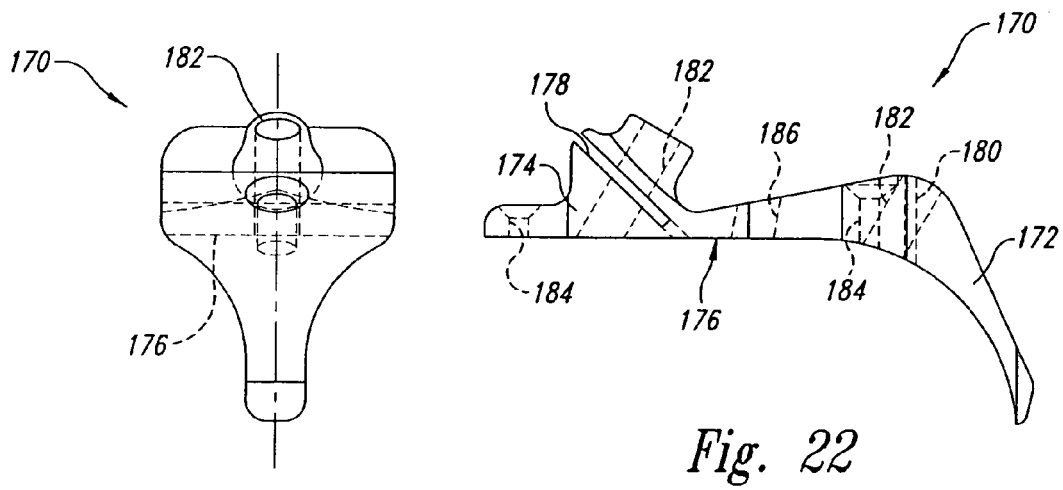
Fig. 23
Fig. 22

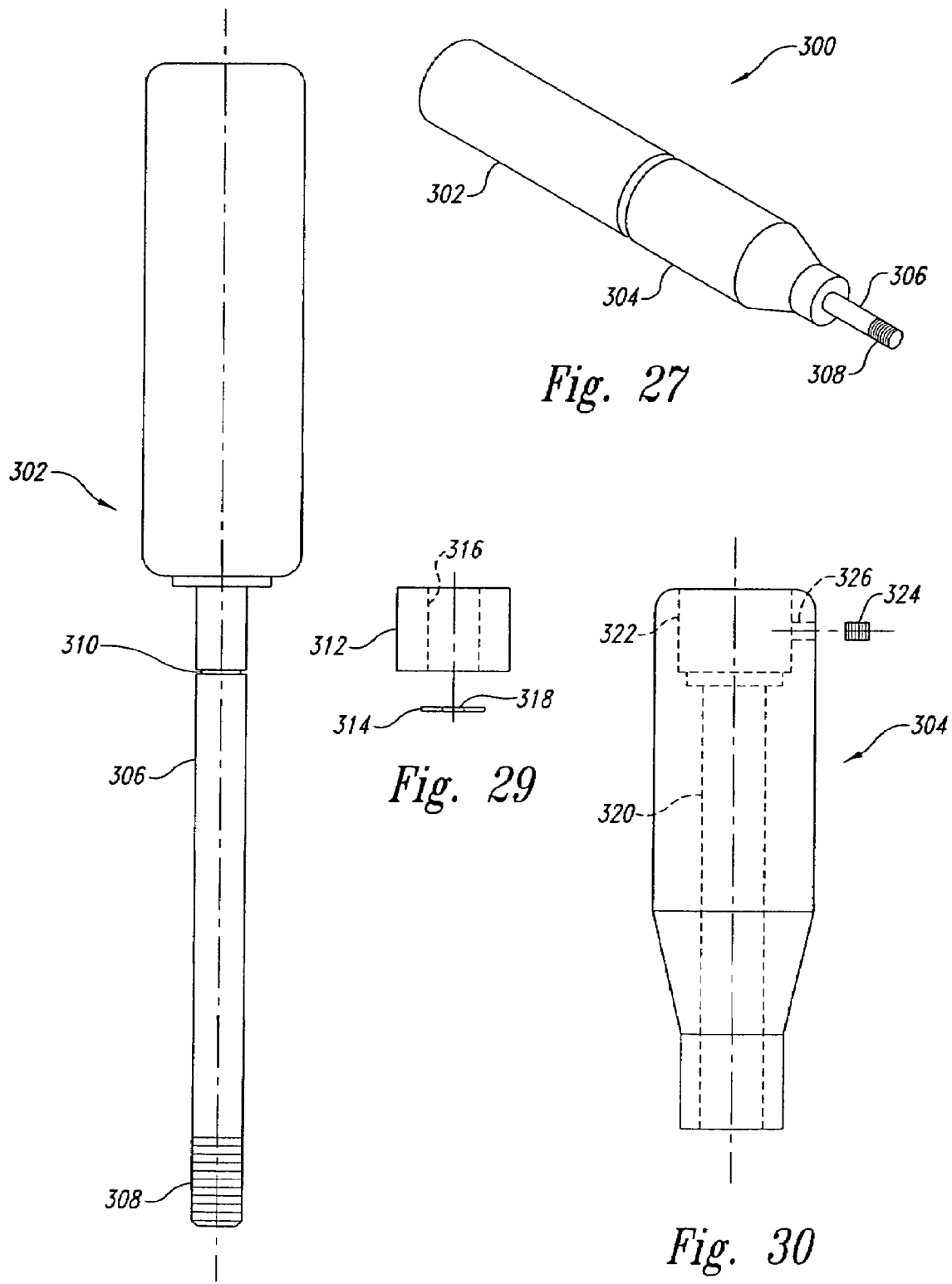

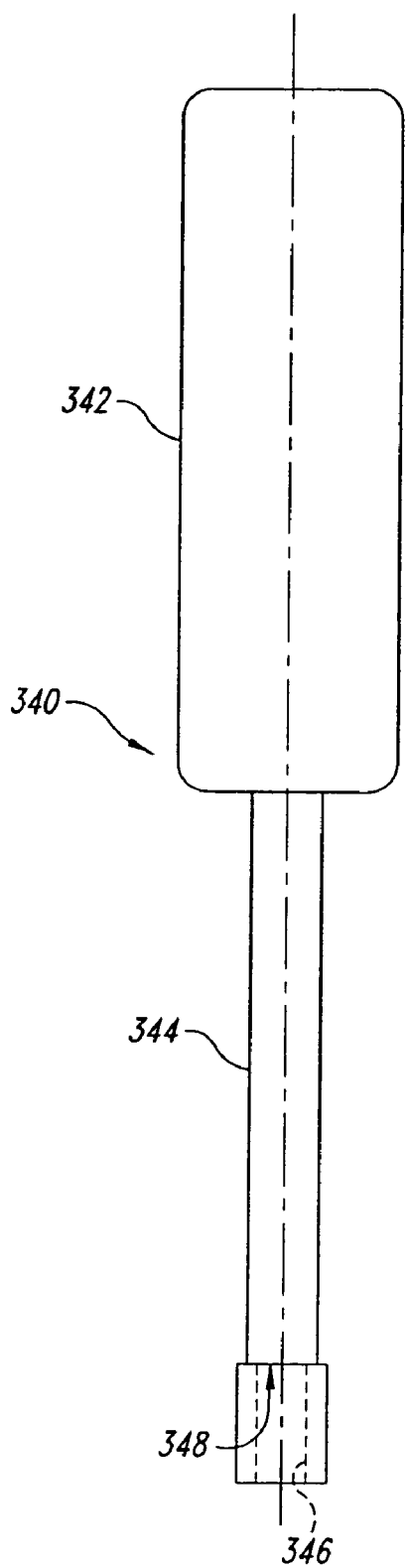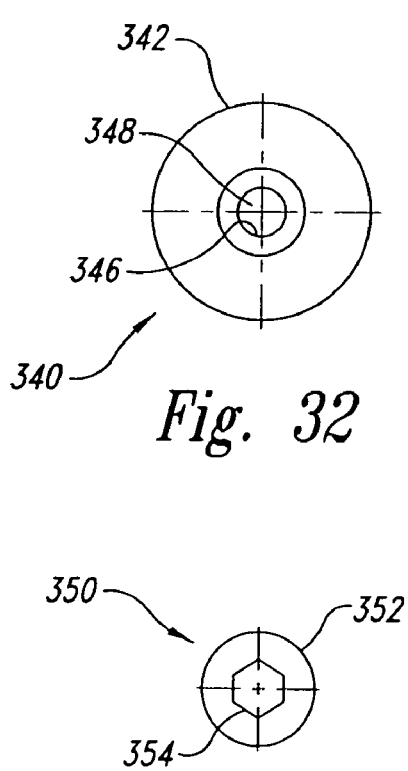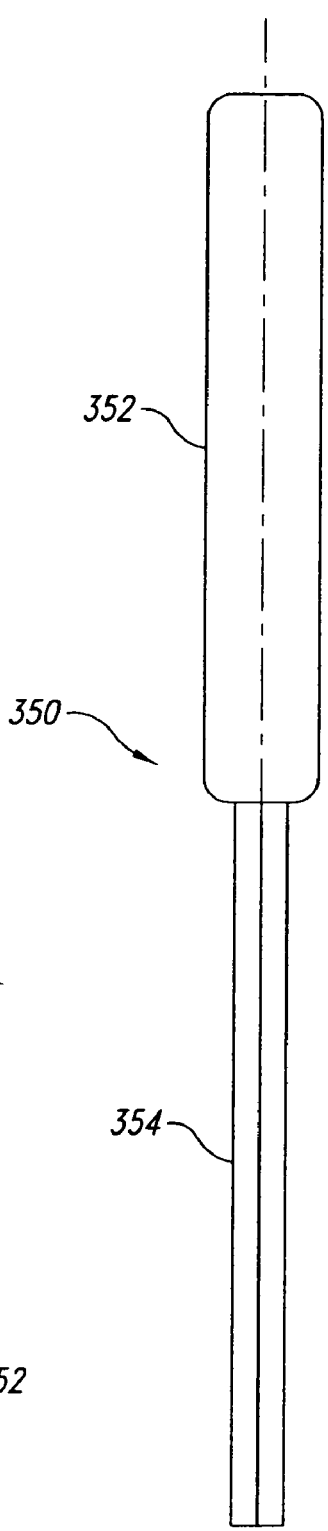
Fig. 31
Fig. 32
Fig. 33
Fig. 34

INSTRUMENTS AND METHODS FOR USE IN PERFORMING KNEE SURGERY

CROSS-REFERENCES TO RELATED APPLICATIONS

This application is a divisional of U.S. patent application Ser. No. 10/151,811, filed May 20, 2002, now U.S. Pat. No. 6,942,700, which is a divisional of U.S. patent application Ser. No. 09/575,691, filed Jun. 29, 2000 and issued on Nov. 12, 2002 as U.S. Pat. No. 6,478,799, where these applications are incorporated herein by reference in their entireties.

BACKGROUND OF THE INVENTION

1. Field of the Invention

The invention relates to surgical apparatus and methods. More particularly, the invention relates to instruments and methods for use during knee replacement procedures.

2. Description of the Related Art

Traditionally, when performing a partial knee replacement procedure, a practitioner first makes a horizontal femoral cut in the distal femur to remove diseased bone and provide a surface for receiving a femoral prosthesis. The proximal tibia is then cut to remove any diseased bone and provide a surface and sufficient clearance for receiving a tibial prosthesis. The femoral and tibial prostheses mate to form a replacement partial knee.

In this traditional procedure, the ultimate alignment of the leg after the prostheses are implanted is determined by the location of the tibial cut with respect to the femoral cut. After the femoral cut has been completed, the practitioner selects the location for the tibial cut based primarily on experience and with the understanding that tibial prostheses are available in a limited number of thicknesses. The tibial cut accordingly is made as close to the proximal end of the tibia as possible, based on how much of the tibia must be removed due to disease, plus whatever additional spacing is required to accommodate the closest standard sized tibial prosthesis. After the tibial cut is made, the prostheses are temporarily implanted and the alignment of the leg is analyzed. To adjust the leg alignment, the practitioner can replace the tibial prosthesis with one of a different thickness, can remove more bone, or can do both. This procedure is followed until the leg is in the desired alignment and balance.

Because the location of the tibial cut is independent of the location of the femoral cut, such a procedure may result in the practitioner making numerous cuts before the desired leg alignment and tension are attained. Also, as a result of this trial-and-error process, practitioners may at times remove more bone than necessary.

One method and instrumentation for making horizontal, femoral and tibial cuts is disclosed in U.S. Pat. Nos. 5,122, 144 and 5,234,433, both to Bert et al. The Bert et al. patents disclose a first instrument for aligning and making the horizontal femoral cut, and a second instrument for aligning and making the horizontal tibial cut.

BRIEF SUMMARY OF THE INVENTION

The present invention relates to instrumentation and methods for use during a knee replacement procedure. In one embodiment of the invention, the instrumentation includes first and second members configured to contact the distal femur and proximal tibia, respectively; an actuator linked to the first and second members; and a cutting guide. The first member is designed to contact either the medial or lateral side of the distal femur and to exert a force on the distal femur in a proximal direction. The second member is designed to contact the corresponding side of the proximal tibia, and to exert a force on the proximal tibia in a distal direction. The second member is movable with respect to the first member to allow a practitioner to rotate the tibia with respect to the femur in the horizontal plane. The actuator is controllable to move the second member, and to retain the second member in a desired position with respect to the first member. Accordingly, the actuator can be manipulated to rotate the tibia with respect to the femur (adjusting the tibiofemoral alignment), and to retain the leg in the desired alignment. The cutting guide is designed to be temporarily fixed to the proximal tibia and the distal femur. The cutting guide has openings therethrough that are sized and shaped to guide a surgical saw for making the horizontal, tibial and femoral cuts.

The system of this embodiment allows the practitioner to position the leg in the alignment that is desired at the end of the implant procedure, and to cut both the femur and the tibia while the leg is fixed in this alignment so that preselected prostheses can be implanted in the knee and the knee will have the desired alignment after the prostheses have been implanted. The distal femoral and proximal tibial cuts can be parallel to each other and perpendicular to the tibial weight-bearing axis. The system may also allow the practitioner to perform the procedure using a smaller incision than that traditionally used, and to avoid excessive bone removal.

In another embodiment of the present invention, the instrumentation has a spacer used in place of the first and second members discussed above. In this particular embodiment, the practitioner has a number of potential spacers available for use, each spacer having a distal end with a distinct thickness. The practitioner can select the desired spacer that creates the preferred leg alignment, then can make the femoral and tibial cuts as described above. As with the previous embodiment, this embodiment allows the practitioner to set the ultimate alignment of the leg prior to making the bone cuts, and to create parallel cuts which are perpendicular to the floor and which avoid excessive bone removal.

In another embodiment, the instrumentation of the present invention incorporates a cutting and drilling guide for use in preparing the distal femur to receive a femoral prosthesis. The cutting and drilling guide has a bottom surface that is shaped to conform with the distal femur after the horizontal femoral cut has been made. The guide has a posterior portion that engages the posterior distal femur, and an anterior portion that mates with the anterior distal femur. The proximal portion is contoured to closely conform with the posterior distal femur to allow the practitioner to flex the leg during the procedure to confirm the guide's alignment. The anterior portion of the guide has a laterally tapered thickness that complements the patella. The guide accordingly can be used without the practitioner first dislocating the patella.

Embodiments of the present invention are also directed to methods for aligning the leg prior to performing knee surgery, methods for aligning the horizontal femoral and tibial cuts, and methods for making both the horizontal tibial and the horizontal femoral cuts using a single guide to create the parallel cuts and the desired, ultimate alignment in the leg. The present invention is also directed toward various combinations of the above instrumentation and methods, as well as the instrumentation and methods used in connection with other such instruments and used in performing other such methods.

BRIEF DESCRIPTION OF THE DRAWINGS

FIG. 3 is a top plan view of the alignment device of FIG. 1.

FIG. 4 is a side elevation view of the alignment device of FIG. 1.

FIG. 5 is a side elevation view of a first member of the alignment device of FIG. 1.

FIG. 6 is a top plan view of the first member of FIG. 5.

FIG. 7 is a side elevation view of a second member of the alignment device of FIG. 1.

FIG. 8 is a top plan view of the second member of FIG. 7.

FIG. 9 is an end view of the alignment element of FIG. 1 shown in a first position.

FIG. 10 is an end view of the alignment device of FIG. 1 shown in a second position.

FIG. 11 is a top plan view of an alignment device according to another embodiment of the present invention.

FIG. 12 is a side elevation view of the alignment device of FIG. 11.

FIG. 13 is an end view of the alignment device of FIG. 11.

FIG. 14 is an end view of a variation of the alignment device shown in FIG. 13.

FIG. 15 is an end view of another variation of the alignment device shown in FIG. 13.

FIG. 21 is a top plan view of a femoral cutting and drilling guide according to one embodiment of the present invention.

FIG. 22 is a side elevation view of the guide of FIG. 21.

FIG. 23 is an end view of the guide of FIG. 21.

FIG. 24 is a sectional end view of the guide of FIG. 21, viewed along Section 24-24.

FIG. 27 is an isometric view of a mounting instrument according to one embodiment of the present invention.

FIG. 28 is a plan view of a driving member from the mounting instrument of FIG. 27.

FIG. 29 is an exploded plan view of a bearing and a circlip from the mounting instrument of FIG. 27.

FIG. 30 is an exploded plan view of a handle and set screw from the mounting instrument of FIG. 27.

FIG. 31 is a plan view of a pin driver according to one embodiment of the present invention.

FIG. 32 is an end view of the pin driver of FIG. 31.

FIG. 33 is a plan view of a nut driver according to one embodiment of the present invention.

FIG. 34 is an end view of the nut driver of FIG. 33.

DETAILED DESCRIPTION OF THE ILLUSTRATED EMBODIMENTS

Figure 1:
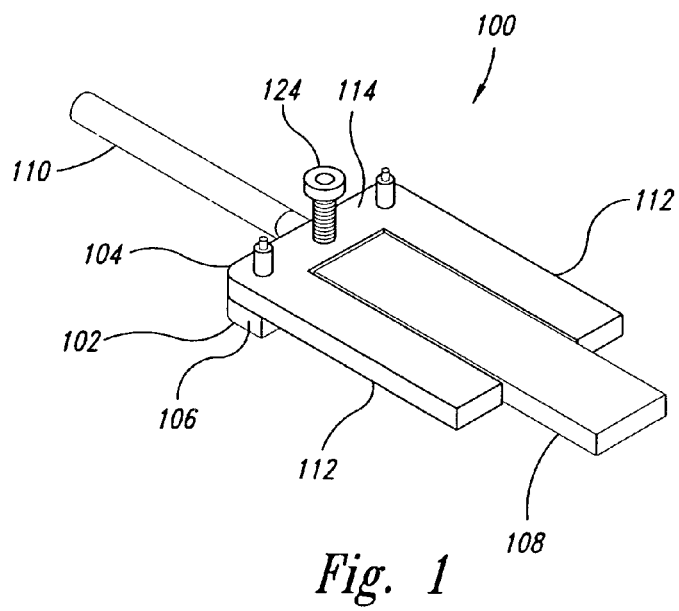
FIG. 1 is an isometric view of an alignment device according to one embodiment of the present invention.

The present invention is generally directed toward instruments for use during knee replacement procedures, and toward methods of using the same. Several embodiments of the invention may allow a medical practitioner to perform a complete unicompartmental knee replacement through a relatively small incision with reduced trauma to the bone and soft tissues, and accordingly may reduce the morbidity, pain and recuperation time to the patient, as well as reducing complications associated with intramedullary guide placement. Embodiments of the present invention may also allow the practitioner to accurately determine the ultimate alignment of the leg prior to making the horizontal, femoral and tibial cuts, and thus may reduce problems or inefficiencies related with the trial-and-error method of the prior art. Embodiments of the invention may also allow the practitioner to make both the horizontal, femoral and tibial cuts using a single cutting guide, and to prepare the distal femur for receiving the implant without dislocating the patella. Many specific details of certain embodiments of the invention are set forth in the following description and in FIGS. 1-46 to provide a thorough understanding of such embodiments. One skilled in the art, however, will understand that the present invention may have additional embodiments, or may be practiced without several of the details described in the following description.

FIGS. 1-4 illustrate an alignment device 100 according to one possible embodiment of the invention, generally incorporating a first member 102 and a second member 104. In the orientation illustrated in FIG. 1, the first member 102 is positioned below the second member 104. The first member 102 has a central body 106, a prong 108 projecting in a distal direction from the central body, and a post 110 projecting in a proximal direction from the central body. The prong 108 is elongated and is offset from the central body 106 of the first member 102 such that the prong is generally aligned with the second member 104.

The post 110 projects from the central body 106 of the first member 102 in a proximal direction that is essentially opposite the direction in which the prong 108 projects. As discussed below, the length and shape of the post 110 is selected to engage with other surgical implements for use in performing the methods of the present invention.

The second member 104 of the illustrated embodiment is a generally U-shaped, flat member having two opposing legs 112 and a base 114 extending between the two legs. The base 114 of the second member 104 is generally aligned with and positioned above the central body 106 of the first member 102. Due to the offset of the prong 108 with respect to the central body 106 of the first member 102, the legs 112 of the second member 104 generally lie in a common plane with the prong. The second member 104 is movable with respect to the first member 102 to cause the legs 112 to move out of this common plane.

Although the alignment device 100 is illustrated with a single prong 108 and a pair of opposing legs 112, it is understood that the first member 102 can have two or more prongs 108, that the second member 104 can have more or a single leg 112, and that the device can have a variety of shapes suitable for performing the methods described below.

FIGS. 5 and 6 further illustrate the first member 102 according to this particular embodiment of the invention. The central body 106 of the illustrated embodiment is integrally formed with the post 110 and the prong 108. The central body 106 projects laterally in opposing directions with respect to the length of the prong 108 and the post 110 (FIG. 6). A rod 116 projects from each of the opposing sides of the central body 106 in an upward direction as illustrated in FIGS. 1 and 5. The rods 116 are substantially smooth, and project approximately ½ inch above the surface of the central body 106. The rods 116 are designed to guide the second member 104 as it moves during operation. It is understood that the rods 116 can take a variety of shapes and sizes, any of which is suitable for this particular function. For example, the rods 116 can have rectilinear or oval cross-sectional shapes.

The prong 108 in the illustrated embodiment is a generally elongated, flat member sized and shaped to be inserted between the distal femur and the proximal tibia. The illustrated prong 108 has a rectangular cross-section with a generally flat upper surface 118 and a generally flat lower surface 120. The illustrated prong 108 is considerably wider than it is tall to provide the prong with sufficient surface area and strength for separating the tibia from the femur. Depending on the material used, however, the thickness and cross-sectional shape of the prong can vary. For example, the prong can have a circular, oval, or square cross-section, or can have a tapered tip to facilitate insertion between the distal femur and proximal tibia.

The post 110 in the illustrated embodiment has a circular cross-section having a diameter of approximately ¼ inch. The size and shape of the post 110 is selected to engage with other instruments discussed below. Accordingly, the sizes and shapes of each of these elements can be varied as necessary and suitable for performing their described functions. The post 110 can similarly be removable from the first member 102 and can be positioned at any location along the central body 106. For example, the post 110 can project from one lateral edge of the central body 106.

FIGS. 7 and 8 further illustrate the second member 104 according to this particular embodiment of the invention. The base 114 of the second member 104 has a threaded hole 122 (FIG. 8) extending through its entire thickness for engagement with a screw 124 (FIG. 2) or similar threaded member. At opposing ends of the base 114, an aperture 126 having a smooth internal sidewall extends through the second member 104. A sleeve 128 is aligned with each aperture 126. The sleeve 128 has a smooth internal sidewall complementary with that of the aperture 126. The apertures 126 and sleeves 128 are aligned to mate with the rods 116 (FIG. 6) on the first member 102. The apertures 126 closely mate with the rods 116 to prevent the second member 104 from rotating over a substantial angle with respect to the first member 102. Although the threaded hole 122 is shown centrally located and the apertures 126 laterally located, it is envisioned that the aperture can be centrally located, and that the threaded hole can be located on one or both of the lateral portions of the central body 106.

Figure 2:
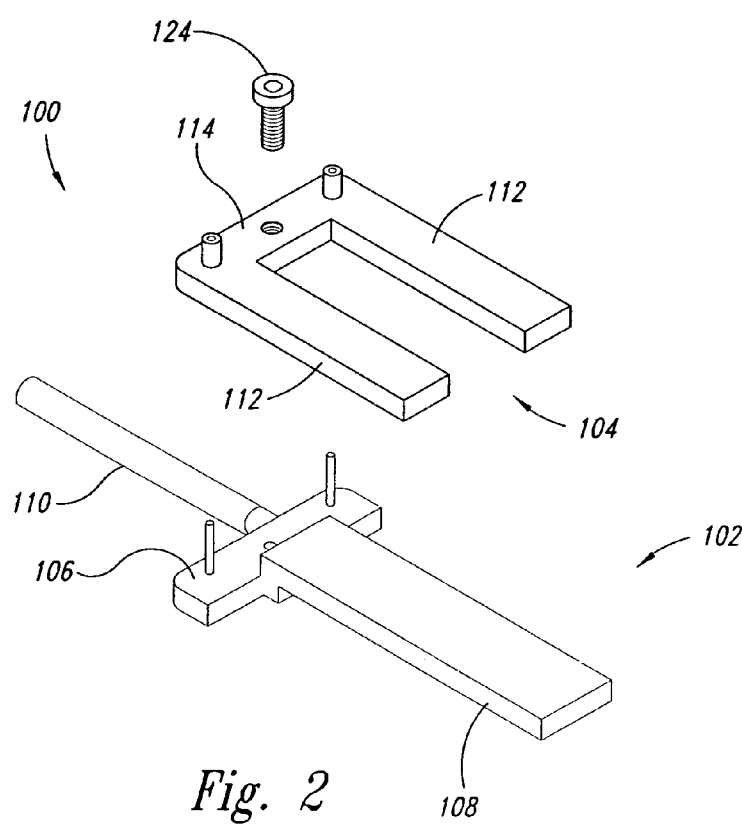
FIG. 2 is an exploded view of the alignment device of FIG. 1.

The legs 112 on the second member 104 are elongated and have a generally rectangular cross-section similar to that of the prong 108 of the first member 102 (FIG. 2). The legs 112 have a top surface 130 and a bottom surface 132. The top and bottom surfaces 130/132 are generally flat and smooth, and are generally aligned to be coplanar with the upper and lower surfaces 118/120 of the prong 108 when the first and second members 102/104 are fully engaged with each other (see FIG. 4). The legs 112 in the illustrated embodiment are shorter than the prong 108 (see FIG. 3). The relative length of the prong 108 and the legs 112 can vary, however, based on the practitioner's needs or other factors.

FIG. 9 illustrates the alignment device 100 configured for insertion between the distal femur and proximal tibia. The screw 124 has been withdrawn from the base 114 by a sufficient distance to allow the base to contact the central body 106. As a result, the prong 108 is generally aligned with the legs 112. The thickness between the lower surface 120 of the prong 108 and the top surfaces 130 of the legs 112 is a minimum thickness "t" in this configuration. This minimum thickness "t" enables the distal end of the alignment device 100 to be slidably inserted between the distal femur and the proximal tibia.

FIG. 10 illustrates the alignment device 100 configured to space the proximal tibia from the distal femur. In this configuration, the screw 124 has been threaded through the base 114 to space the base apart from the central body 106. As a result, the lower surface 120 of the prong 108 is spaced apart from the top surfaces 130 of the legs 112 by an increased thickness "T." As the screw 124 is threaded into the base 114, the increased thickness "T" further increases to further space the tibia apart from the femur.

Embodiments of the alignment device 100 may have many advantages over instruments of the prior art. For example, the alignment device 100 may allow a practitioner to rotate a patient's tibia in the horizontal plane relative to the femur to position the leg in the desired alignment prior to making the bone cuts necessary for implanting prostheses. As a result, the practitioner may be better able to create the desired ultimate alignment in the patient's leg after implant. In addition, the practitioner may be able to perform the procedure making fewer cuts and, consequently, remove the least amount of bone necessary.

FIGS. 11-13 illustrate a spacer 140 according to another embodiment of the present invention. The spacer has a distal portion 142 and a proximal portion 144. The distal portion 142 has a rectilinear cross-section and is substantially wider than it is thick to allow the spacer to be inserted between the distal femur and the proximal tibia. The distal portion has a thickness "d1" (FIG. 13). The proximal portion 144 of the spacer 140 has a size and shape similar to the post 110 described in the above embodiment.

FIGS. 14 and 15 show other variations of spacers 140a/140b, respectively. The spacer 140a is generally sized and shaped similar to spacer 140 described above. A distal end 142a of spacer 140a, however, has an increased thickness "d2" (FIG. 14) that is slightly larger than thickness "d1" of the previous spacer. Similarly, a distal end 142b of spacer 140b has a further increased thickness "d3" (FIG. 15) that is larger than increased thickness "d2."

Embodiments of the spacers 140/140a/140b have a number of advantages over the prior art. For example, a practitioner can insert one of a number of spacers between a patient's distal femur and proximal tibia to create the desired alignment in the patient's leg prior to making any bone cuts necessary for implanting prostheses.

Figure 16:
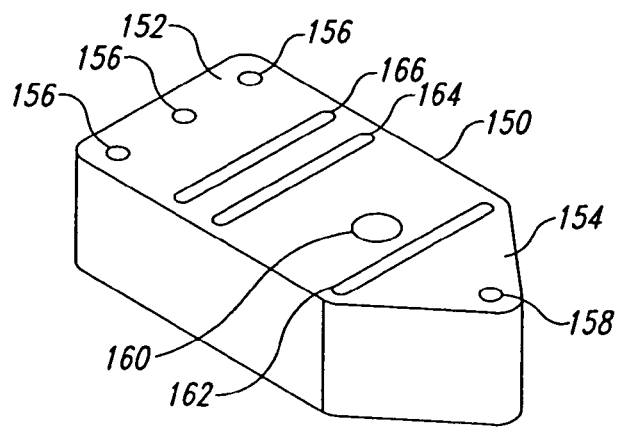
FIG. 16 is an isometric view of a cutting guide according to one embodiment of the present invention.
Figure 17:
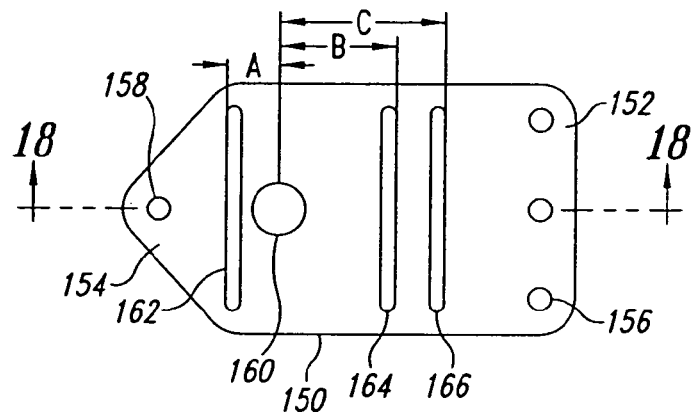
FIG. 17 is a top plan view of the cutting guide of FIG. 16.
Figure 18:
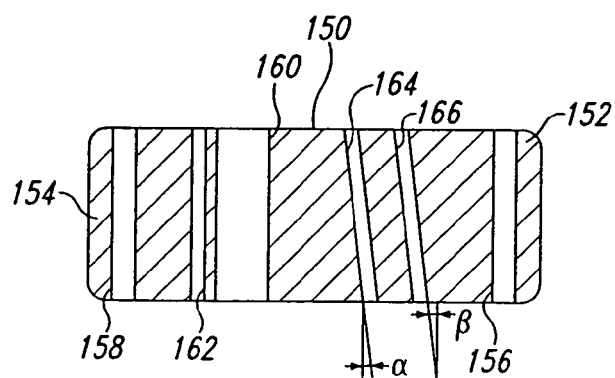
FIG. 18 is a sectional side elevation view of the cutting guide of FIG. 17, viewed along Section 18-18.

FIGS. 16-18 illustrate a cutting guide 150 according to one particular embodiment of the present invention. The cutting guide 150 has a generally block-shaped body with a tibial end 152 and an opposing femoral end 154. The tibial end 152 of the cutting guide 150 terminates in a generally flat surface with rounded corners. Three tibial pin guides 156 are distributed along the tibial end 152 of the cutting guide 150. Each of the tibial pin guides 156 extends through the cutting guide 150, and is sized to closely receive a standard surgical pin for fixing the cutting guide to the proximal end of the tibia.

The femoral end 154 of the cutting guide 150 terminates in a generally triangular end portion with a rounded apex. A single femoral pin guide 158 is located near the femoral end 154 of the cutting guide 150. Similar to the tibial pin guides 156, the femoral pin guide 158 extends through the cutting guide 150, and is shaped to receive a surgical pin for fixing the cutting guide to the femur. It is understood that the number and arrangement of the tibial pin guides 156 and femoral pin guides 158, as well as the general shapes of the tibial end 152 and femoral end 154 of the cutting guide 150, can vary significantly without affecting the function of the cutting guide 150. For example, the cutting guide 150 can have a rectilinear or oval overall shape, and more or fewer pins can be used for particular procedures or particular practitioners, as desired or as otherwise required. Similarly, the size or shape of the tibial pin guides 156 and/or femoral pin guides 158 can be modified to receive screws or other fasteners.

Figure 19:
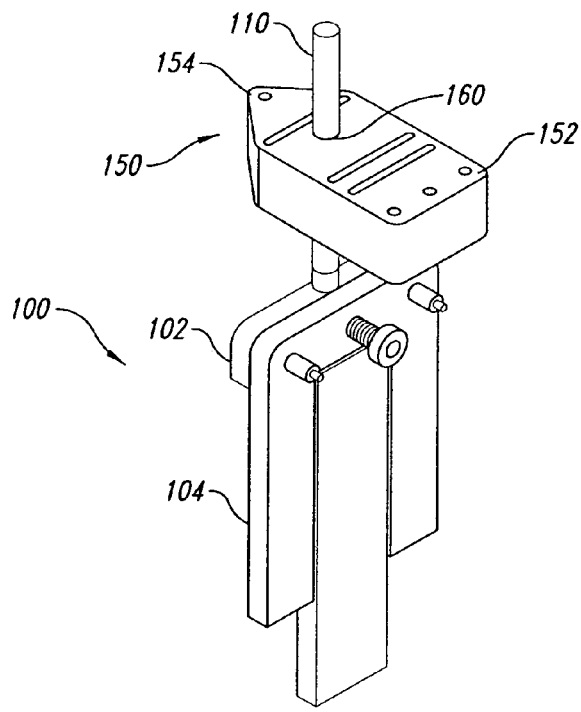
FIG. 19 is an isometric view of a combination of an alignment device and a cutting guide according to one embodiment of the present invention.

A mounting opening 160 is centrally located on the cutting guide 150. The mounting opening 160 has a circular cross-sectional shape and extends through the entire thickness of the cutting guide 150. The mounting opening 160 is slightly larger than the post 110 projecting from the central body 106 of the first member 102 (FIG. 1). Accordingly, the cutting guide 150 can be mounted on the post 110, as illustrated in FIG. 19. The cutting guide 150 can be rotated about the post 110 to allow the practitioner to change the alignment of the cutting guide with respect to the patient's leg, as desired.

A first tibial cutting groove 164 and a second tibial cutting groove 166 are positioned between the mounting opening 160 and the tibial end 152 of the cutting guide 150. As best illustrated in FIG. 18, the first and second tibial cutting grooves 164/166 extend through the cutting guide 150 at approximately a 7 degree angle of declination (angles "α" and "β"). The tibial cutting grooves 164/166 are sufficiently wide and tall to receive a surgical cutting saw, and to direct the saw into the proximal tibia for making what is generally referred to as the horizontal tibial cut. It is envisioned that the tibial cutting grooves 164/166 can be oriented at different angles with respect to the cutting guide 150. For example, the tibial cutting grooves 164/166 can be perpendicular to the length of the cutting guide 150, or can be at a lesser or greater angle than the illustrated 7 degrees.

A femoral cutting groove 162 is located between the mounting opening 160 and the femoral end 154 of the cutting guide 150. The femoral cutting groove 162 is generally sized and shaped the same as the tibial cutting grooves 164/166 to receive the saw. The femoral cutting groove 162, however, is oriented perpendicular to the length of the cutting guide 150. The femoral cutting groove 162 is oriented to guide the saw to make what is generally known as the horizontal femoral cut. As with the tibial cutting grooves 164/166, the femoral cutting groove 162 can be angled with respect to the cutting guide 150.

As best illustrated in FIG. 17, the femoral cutting groove 162 is located to position the horizontal femoral cut approximately 3.5 millimeters from the centerline of the mounting opening 160 (distance "A"). As illustrated in FIGS. 9 and 10, the centerline of the post 110, which is colinear with the centerline of the mounting opening, is aligned with the lower surface 120 of the prong 108. Consequently, when the alignment device 100 is inserted between the distal femur and the proximal tibia with the lower surface 120 in contact with the distal femur, the centerline of the mounting opening 160 is aligned with the distal end of the femur. A cut made using the femoral cutting groove 162 will accordingly remove approximately 3.5 millimeters of bone from the distal end of the femur. This thickness is selected due to the currently standard thickness of a femoral prosthesis. The distance "A" between the mounting opening 160 and the femoral cutting groove 162 can vary to accommodate different implants.

Returning to FIG. 17, the first tibial cutting groove 164 is located to position the horizontal tibial cut eight millimeters from the distal end of the femur (distance "B"), and the second tibial cutting groove 166 is located to position the horizontal tibial cut ten millimeters from the distal end of the femur (distance "C"). These two dimensions are consistent with two currently standard thicknesses of tibial plates used in tibial prostheses. The "B" and "C" distances can vary, however, as necessary to accommodate particular prostheses or the particular needs or desires of the practitioner. For example, the first and second tibial cutting guides can be 12 and 14 millimeters from the distal end of the femur, or can include various combinations of these distances.

FIG. 19 illustrates one possible combination of the alignment device 100 and the cutting guide 150 of the present invention. When configured for a procedure, the femoral end 154 of the cutting guide 150 is positioned on the side of the first member 102 of the alignment device 100 and the tibial end 152 of the cutting guide 150 is positioned on the side of the second member 104 of the alignment device 100. It is envisioned that this orientation can be changed.

Figure 20:
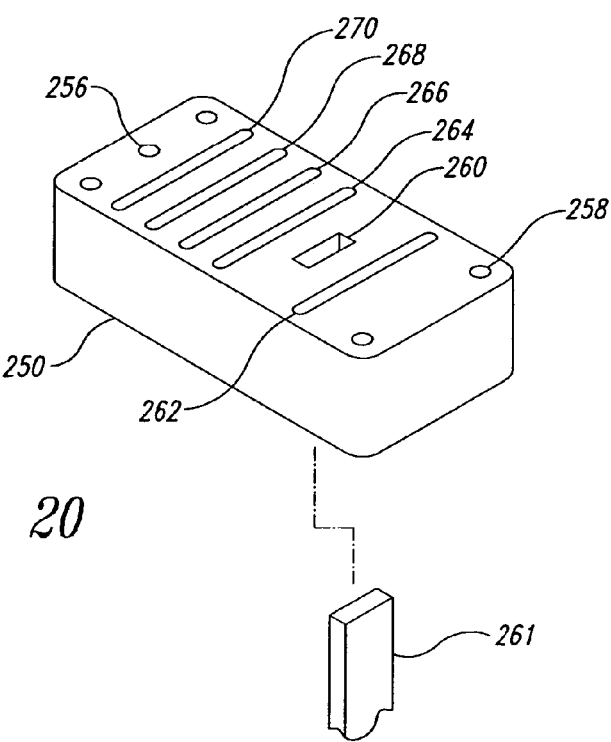
FIG. 20 is an exploded isometric view of another cutting guide and a portion of another alignment device according to another embodiment of the present invention.

FIG. 20 illustrates another cutting guide 250 according to another embodiment of the present invention. The cutting guide 250 of this particular embodiment has a number of tibial pin guides 256 and a number of femoral pin guides 258, similar to those defined in connection with previous embodiment. In this particular embodiment, however, there are three evenly spaced tibial pin guides 256 and two femoral pin guides 258.

The cutting guide 250 has a mounting opening 260 for receiving a complementary mounting post 261 on an alignment device. The mounting opening 260 has a rectilinear cross-section that is sized to closely receive the complementary mounting post 261. Because the mounting opening 260 and mounting post 261 are rectilinear, the cutting guide 250 will not rotate over a substantial angle with respect to the alignment device. Consequently, the practitioner can engage the cutting guide 250 with an alignment device and avoid the task of aligning the cutting guide with a patient's leg. The orientation of the mounting opening 260 and/or the post 261 can vary.

The cutting guide has a femoral cutting groove 262 for cutting the distal end of the patient's femur. The femoral cutting groove 262 is substantially the same as that described in connection with the previous embodiment.

The cutting guide 250 also has four tibial cutting grooves 264/266/268/270. The four tibial cutting grooves 264/266/268/270 are spaced apart to provide the practitioner with a number of options for making the horizontal tibial cut. For example, the tibial cutting grooves can be spaced 8, 10, 12 and 14 millimeters from the distal end of the femur, respectively.

FIGS. 21-24 illustrate a low profile cutting/drilling guide 170 for use in making the cuts and drilling the holes in the distal femur necessary for the femur to receive the trial femoral implant 200 or a currently standard femoral prosthesis. The cutting/drilling guide 170 has a distal portion 172 that aligns with the posterior portion of the condyle being operated upon; a proximal portion 174 opposite the distal portion; and a lower surface 176 shaped to generally mate with the contour of the condyle after the horizontal femoral cut has been made.

The cutting/drilling guide 170 has a bevel cut guide 178 aligned to guide the practitioner in making the superior posterior chamfer cut; and a posterior cut guide 180 aligned to assist the practitioner in making the posterior articulating surface cut. The cutting/drilling guide 170 also has a pair of mounting hole guides 182 aligned to assist the practitioner in drilling the mounting holes for the femoral implant. The bevel cut guide 178, the posterior cut guide 180 and the mounting hole guides 182 are generally sized and oriented to mount both the currently standard femoral prosthesis and the trial femoral implant 200 discussed below. The spacing, alignment and/or size of each of the cutting and drilling guides, however, can be modified to accommodate any similar implant currently being marketed or developed in the future.

The cutting/drilling guide 170 also has a number of pinholes 184 sized and aligned to direct either surgical pins or fixation screws into the distal femur to retain the guide during the cutting and drilling portions of the procedure. In the illustrated embodiment, the pinholes 184 are located within the boundary of the cutting/drilling guide 170. The particular placement and size of the pinholes 184 on the cutting/drilling guide 170 can vary based on whether the procedure will be performed on the medial or lateral condyle, or based on practitioner preference or other factors. In the illustrated embodiment, two pinholes 184 are located near the distal portion 172 to align with the posterior distal femur, and one pinhole 184 is located near the proximal portion 174.

A threaded opening 186 is centrally located between the proximal and distal portions 174/172 of the cutting/drilling guide 170. The threaded opening 186 is sized and configured to mate with a threaded mounting instrument 300 (FIG. 27) to assist the practitioner in placing the cutting/drilling guide 170 in the desired location, and in retaining the guide firmly against the femur while it is being fixed thereto. The threaded opening 186 can be in a different location or alignment on the cutting/drilling guide 170, can have different shapes or sizes, or can use different fasteners generally suitable for its described function. After the practitioner has placed the cutting/drilling guide 170 against the distal femur and has removed the threaded mounting instrument 300, the practitioner can peer through the threaded opening 186 to confirm that the guide is properly seated on the distal femur.

As best illustrated in FIG. 22, the thickness of the cutting/drilling guide 170 is substantially reduced as compared to cutting and/or drilling guides of the prior art. In the illustrated embodiment, the thickness of the cutting/drilling guide 170 is no greater than 15 mm, and preferably 1 cm. The distal portion 172 of the guide is even further reduced in thickness to allow the leg to be extended while the guide is mounted on the leg to allow the practitioner to confirm that the guide is mounted properly. In the illustrated embodiment, the thickness of the distal portion (i.e., the portion distally located with respect to the posterior cut guide 180) is no greater than 1 cm, and is preferably no greater than 5 mm. In some embodiments, it is envisioned that the thickness of the distal portion 172 can be no greater than 1-1.5 mm.

The proximal portion 174 of the guide 170 has two opposing tapered surfaces 183, each extending laterally from the mounting guide hole 182. The tapered surfaces 183 are substantially reduced in thickness and tapered to provide room for the patella during the procedure.

The cutting/drilling guide 170 of the present invention may have a number of advantages over instruments of the prior art. For example, the reduced thickness and contoured shape of the guide allows the practitioner to perform this portion of the procedure through an incision considerably smaller than required by prior art methods and instrumentation. These features also provide the practitioner with an unobstructed view of the distal femur to confirm that the guide is properly seated before making the cuts and drilling the holes.

Unlike prior art cutting and drilling guides, which are commonly designed for full arthrotomy, the cutting/drilling guide 170 of the present invention allows the practitioner to perform this portion of the procedure without dislocating the kneecap. The low profile and contour of the cutting/drilling guide 170 may also allow the practitioner to better view the procedure and to range the knee with the block in place to verify appropriate block fixation.

Figure 25:
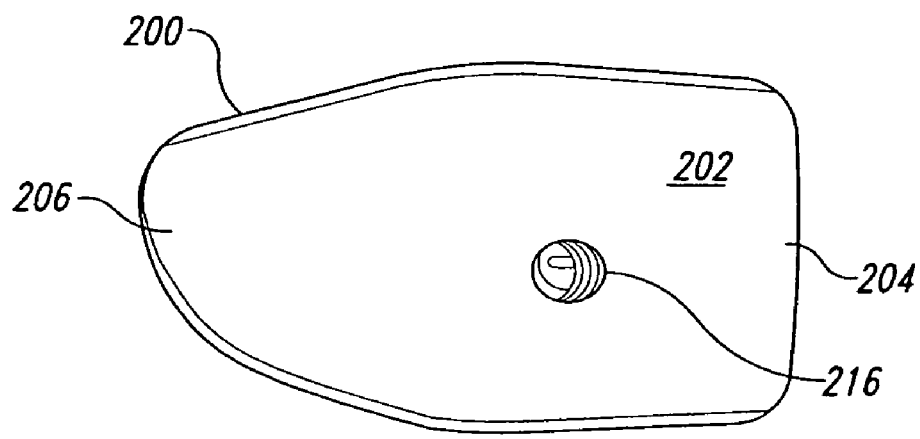
FIG. 25 is a top plan view of a femoral implant according to one embodiment of the present invention.
Figure 26:
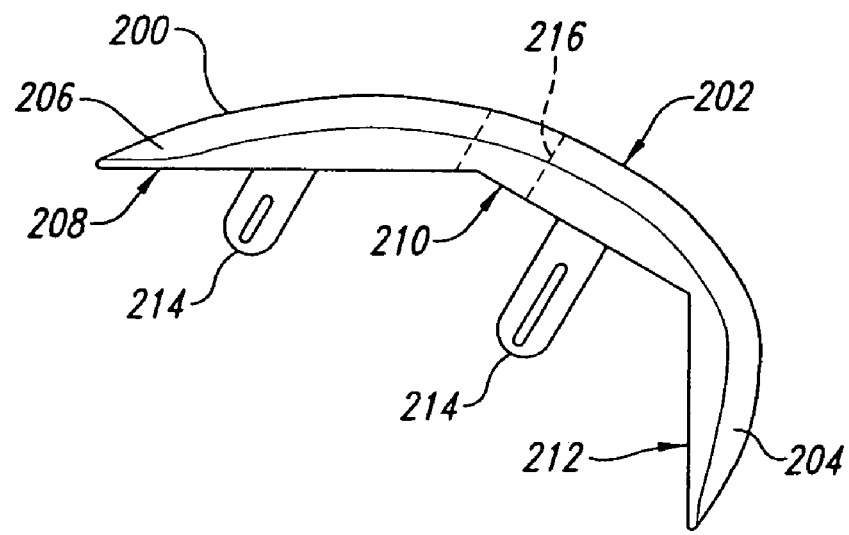
FIG. 26 is a side elevation view of the femoral implant of FIG. 25.

FIGS. 25 and 26 illustrate a trial femoral implant 200 according to one particular embodiment of the present invention. The trial femoral implant 200 has a smooth, curving outer surface 202 designed to engage a complementary tibial implant (not shown). The outer surface 202 extends between a distal end 204 that aligns with the posterior face of the condyle being replaced, and a proximal end 206 that aligns with the anterior portion of the condyle. Opposite the outer surface 202, the trial femoral implant 200 has a proximal inner surface 208 that mates with the surface created by the horizontal femoral cut; a central inner surface 210 that mates with the femoral surface created by the superior posterior chamfer cut; and a distal inner surface 212 that mates with the femoral surface created by the posterior articulating surface cut. The trial femoral implant 200 also has a pair of mounting projections 214 that engage the mounting holes in the distal femur that are drilled using the mounting hole guides 182 in the cutting/drilling guide 170 (FIG. 22).

A threaded hole 216 is bored through a central portion of the femoral implant 200 between the outer surface 202 and the central and proximal inner surfaces 208/210. The threaded hole 216 is sized and threaded to engage the threaded mounting instrument 300 that engages the cutting/drilling guide 170 (FIG. 27). The threaded hole 216 is aligned to allow the practitioner to engage the trial femoral implant 200 with the prepared distal femur, and to urge the implant against the femur during the implant process. Once the trial femoral implant 200 has been fixed to the femur, the threaded mounting instrument 300 can be removed from the implant by unthreading the instrument and, thus, without pulling the implant away from the bone. The size, orientation, thread gage and pitch, and placement of the threaded hole 216 can vary depending on the particular condyle to which the trial femoral implant 200 will be attached, or based on practitioner preferences or other factors.

FIG. 27 illustrates a mounting instrument 300 according to one particular embodiment of the present invention. The mounting instrument 300 can be used to mount the cutting/drilling guide 170 and/or the trial femoral implant 200 of the present invention. The mounting instrument 300 incorporates a driving member 302 and a handle 304. The driving member 302 is an elongated, cylindrical member, and has a shaft 306 projecting therefrom, which terminates at a threaded end 308. The shaft 306 extends through the handle 304 and can rotate with respect to the handle during use. As further illustrated in FIG. 28, the shaft 306 has an annular groove 310 cut into its outer surface at a location approximately ¾ inch from the shaft's proximal end.

FIG. 29 illustrates a bearing 312 and a circlip 314 that together allow the handle 304 to rotate smoothly with respect to the driving member 302 while preventing the handle from slipping off the shaft 306. The bearing 312 has a bore 316 extending therethrough. The bore 316 has a diameter approximately equal to the diameter of the shaft 306. The circlip 314 has a reduced diameter bore 318 therethrough for engagement with the annular groove 310 in the shaft 306. With the bearing 312 slid onto the shaft 306 beyond the annular groove 310, the circlip 314 can be attached to the shaft 306 to retain the bearing on the shaft.

FIG. 30 further illustrates the handle 304 of the mounting instrument 300. The handle 304 has an elongated, tubular channel 320 extending substantially its entire length. The channel 320 has a diameter slightly larger than that of the shaft 306 to allow the shaft to freely rotate within the channel. One end of the handle 304 has an increased diameter bore 322 extending approximately ¾ inch into the end of the handle. The diameter of the increased diameter bore 322 is sized and shaped to complement the shape of the bearing 312 such that the bearing can be received within the increased diameter bore. A set screw 324 can be threaded into a set screw opening 326 in the handle 304. The set screw opening 326 is positioned to cause the set screw 324 to impinge upon the bearing 312 when the bearing is fully inserted into the increased diameter bore 322. As a result, when the bearing 312 is fully engaged with the shaft 306, the circlip 314 is engaged with the annular groove 310, the handle 304 is fully engaged with the bearing 312, and the set screw 324 is fully engaged with the set screw opening 326, the mounting instrument is operable such that the driving member 302 can rotate with respect to the handle 304 but the handle 304 cannot slide off of the shaft.

Embodiments of the mounting instrument 300 have numerous advantages over the prior art. For example, the mounting instrument 300 can be engaged with a cutting/drilling guide 170 or a trial femoral implant 200 to assist the practitioner in orienting the guide or prosthesis, urging it against the distal femur, and retaining it in position during portions of the procedure. The practitioner can urge the handle 304 toward the distal femur to maintain the guide or prosthesis against the distal femur, while simultaneously rotating the driving member 302 to remove the threaded end 308 of the shaft 306 from the guide or prosthesis. This may allow the practitioner to remove the mounting instrument 300 from the guide or prosthesis without exerting a tensile force on the guide or prosthesis, reducing the likelihood that the guide or prosthesis will be prematurely moved or removed from the distal femur.

FIGS. 31 and 32 illustrate a pin driver 340 according to one particular embodiment of the present invention. The pin driver 340 incorporates the handle 342 and an elongated shaft 344 projecting from one end of the handle. At the end of the shaft 344 opposite the handle 342, a hollow 346 is formed extending into the shaft 344 a portion of the distance toward the handle 342. In the illustrated embodiment, the hollow 346 extends approximately ½ inch into the shaft 344 and terminates at a substantially flat bottom surface 348. The illustrated hollow 346 has a circular cross-section that is slightly larger in diameter than a standard surgical pin. Accordingly, the head of a surgical pin can be inserted into the hollow 346 until the pin contacts the bottom surface 348. The end of the handle 342 opposite the shaft 344 is flat to allow the pin driver 340 to be struck by a hammer or similar tool to drive the surgical pin into the bone.

FIGS. 33 and 34 illustrate a nut driver 350 according to one particular embodiment of the present invention. The nut driver has an elongated handle 352 attached to an elongated shaft 354 that projects from the handle. The handle 352 can have a cylindrical shape, can be smooth, rough or otherwise finished to improve grip, or can be shaped similar to a traditional screwdriver. The shaft 354 in the illustrated embodiment is shaped to engage a nut or other fastener having an Allen head. The shaft 354, however, can have a wide variety of shapes for engagement with a wide variety of nuts or other fasteners.

Figure 35:
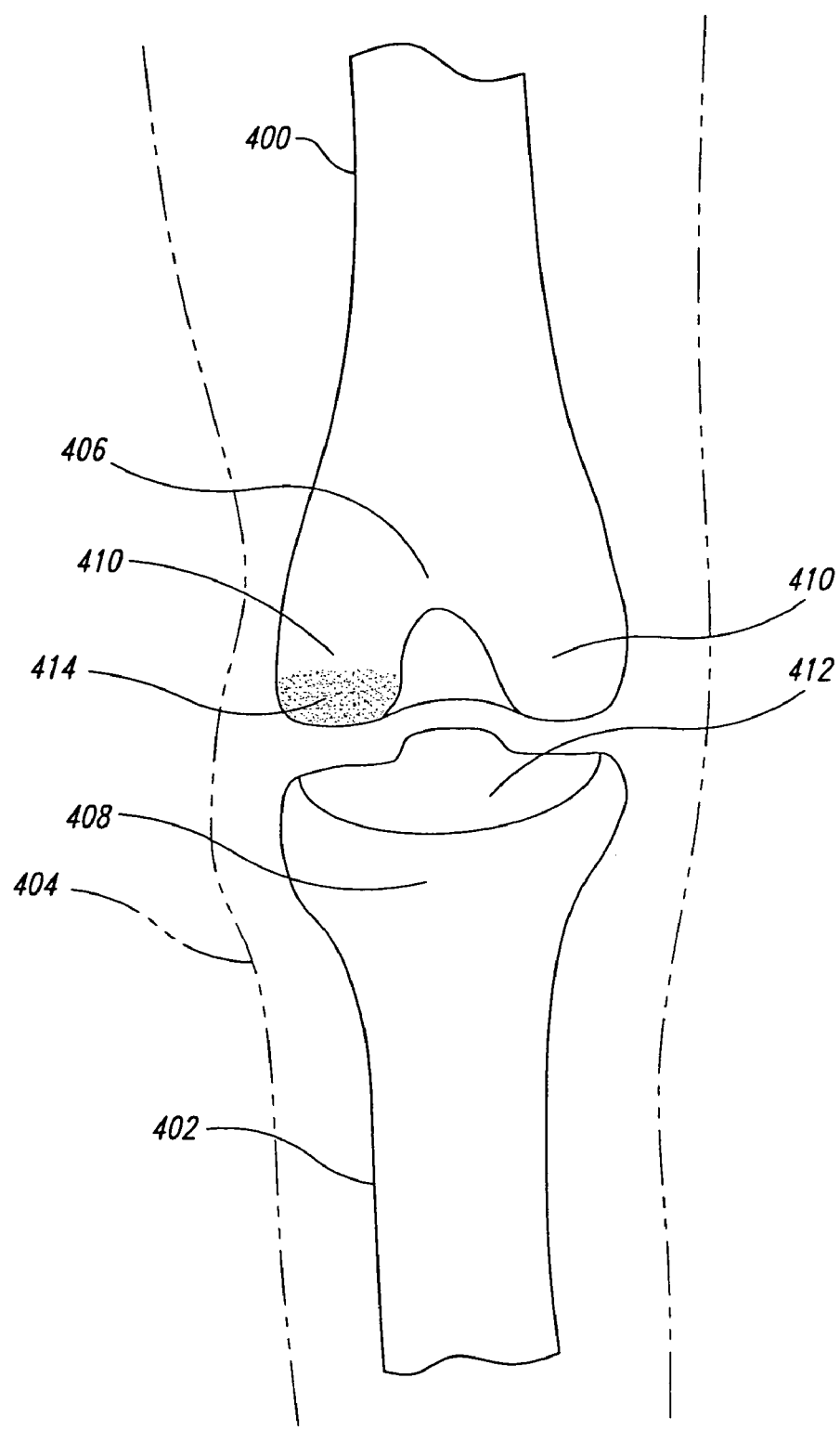
FIG. 35 is a schematic isometric view of a knee—minus the patella—prior to the procedure of the present invention.

FIGS. 35 through 40 illustrate a method for creating a desired alignment in a knee, and for making the horizontal, tibial and femoral cuts of a knee replacement procedure, according to one particular embodiment of the present invention. FIG. 35 shows portions of a femur 400 and a tibia 402 from a leg 404 prior to the method of the present invention. A distal femur 406 abuts a proximal tibia 408, the distal femur terminating in a pair of condyles 410 which contact a tibial plateau 412 at the extreme proximal tibia 408. The method described in this particular embodiment of the present invention is applicable to both the medial and a lateral condyle and, accordingly, the illustrated leg can be the patient's left or right leg. The condyle 410 located on the left side of the illustration in FIG. 35 has a portion of diseased bone 414. The primary purpose of the procedure of this embodiment of the present invention is to remove the diseased bone 414 from the condyle 410, and to replace the removed bone with a femoral prosthesis. As part of this procedure, a portion of the tibial plateau 412 will also be removed to provide a surface and space for a tibial prosthesis that engages the femoral prosthesis.

Figure 36:
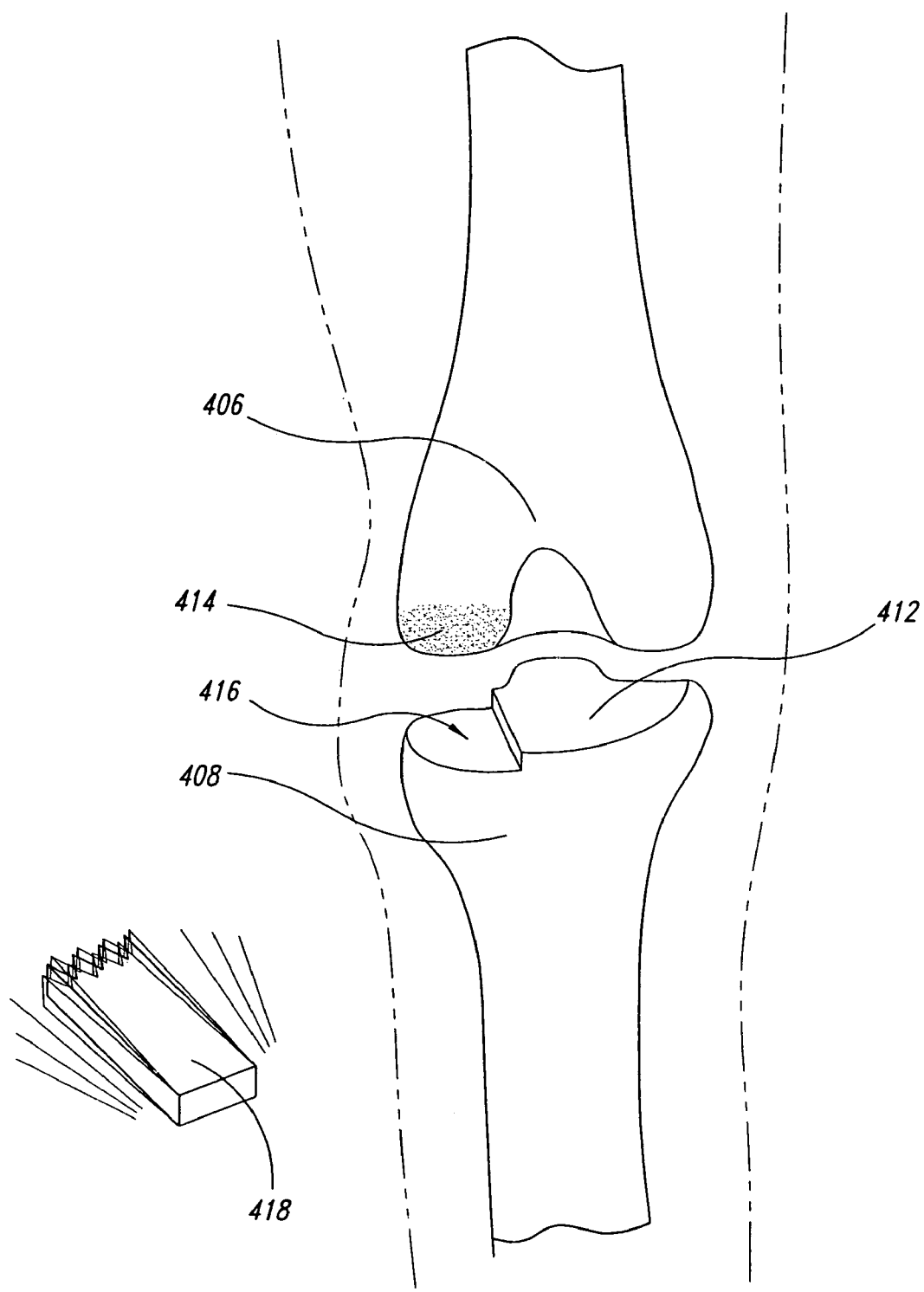
FIG. 36 is a schematic isometric view of the knee of FIG. 35 after a preliminary tibial cut has been made.

FIG. 36 illustrates the distal femur 406 and the proximal tibia 408 after the tibial plateau 412 has been prepared for this particular method of the present invention. A portion of the tibial plateau 412 on the side with the diseased bone 414 on the distal femur 406 has been cut away to provide a flat surface 416. The flat surface 416 can be made using a standard surgical saw 418. The practitioner can make a conservative cut in the proximal tibia 408 to create the flat surface 416, but which removes less bone than necessary for even the thinnest tibial prosthesis. This cut provides a flat surface to receive the alignment device or the spacer. Accordingly, the practitioner may not be at risk for removing more bone than necessary.

Figure 37:
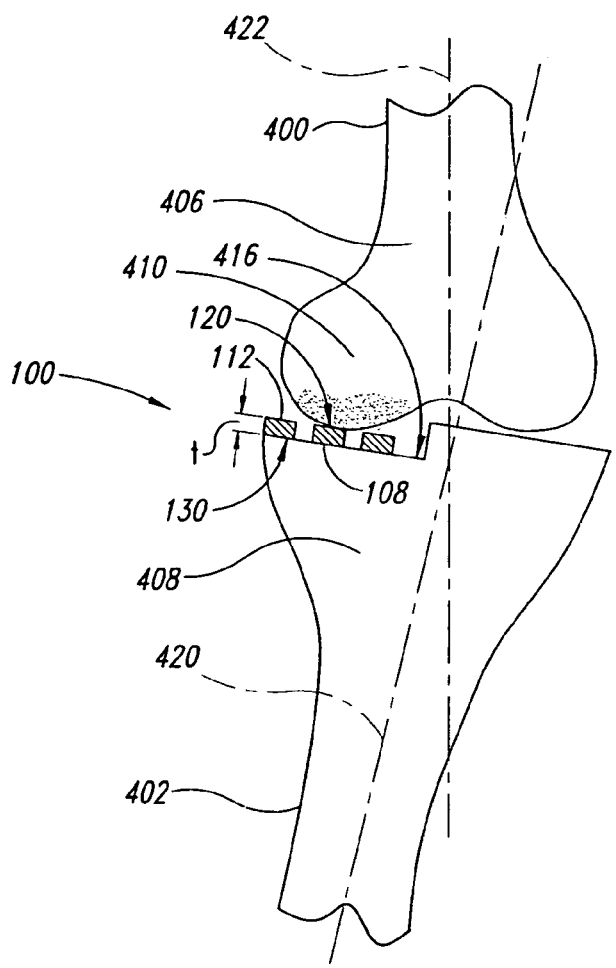
FIG. 37 is a front elevation view of the knee of FIG. 36 after an alignment device according to one embodiment of the present invention has been inserted between the femur and the tibia.

After the flat surface 416 has been created, the practitioner can insert an alignment device or spacer, such as the one described above, between the distal femur 406 and the proximal tibia 408. As illustrated in FIG. 37, an alignment device 100 has been slid between the condyle 410 on the distal femur 406 and the flat surface 416 on the proximal tibia 408. In the illustrated configuration, the alignment device 100 is in the closed position such that the distance between the lower surface 120 of the prong 108 and the top surface 130 of the leg 112 is at the minimum thickness "t" (note: the alignment device 100 is inverted in FIGS. 37-40 compared to that shown in FIG. 1). Because of the bone and cartilage loss associated with the presenting disease and the minimal bone removed to create the flat surface, a tibial axis 420 extending along a length of the tibia 402 is out of alignment with respect to a femoral axis 422 extending along the length of the femur 400. To correct the alignment of the tibial and femoral axes 420/422, the practitioner can rotate the screw 124 to space the second member 104 of the alignment device 100 apart from the first member 102 (as illustrated in FIG. 10).

Figure 38:
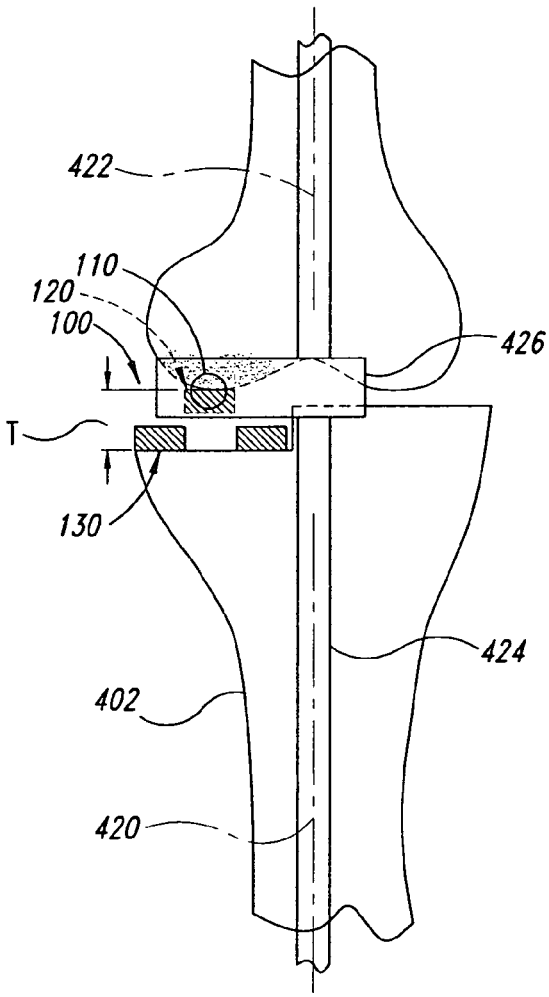
FIG. 38 is a front elevation view of the knee of FIG. 37 after the alignment device has been manipulated, and an alignment rod according to one embodiment of the present invention.

FIG. 38 illustrates the leg 404 after the practitioner has manipulated the alignment device 100 to align the tibial axis 420 with the femoral axis 422. To achieve this configuration, the alignment device 100 is spread apart until the lower surface 120 is spaced apart from the top surface 130 by the increased thickness "T." As the practitioner manipulates the alignment device 100 to move the tibia 402 between the alignment illustrated in FIG. 37 and that illustrated in FIG. 38, the alignment device urges the tibia apart from the femur 400. The alignment can then be adjusted to practitioner preference, which may not always result in the tibial axis 420 being exactly colinear with the femoral axis 422. An alignment rod 424 can be connected by an alignment block 426 to the post 110 on the alignment device 100. The practitioner can use the alignment rod 424 to visually confirm that the leg 404 is in the desired alignment. Once the tibia 402 is in the desired alignment, the practitioner can remove the alignment rod 424 and alignment block 426 from the post 110.

Figure 39:
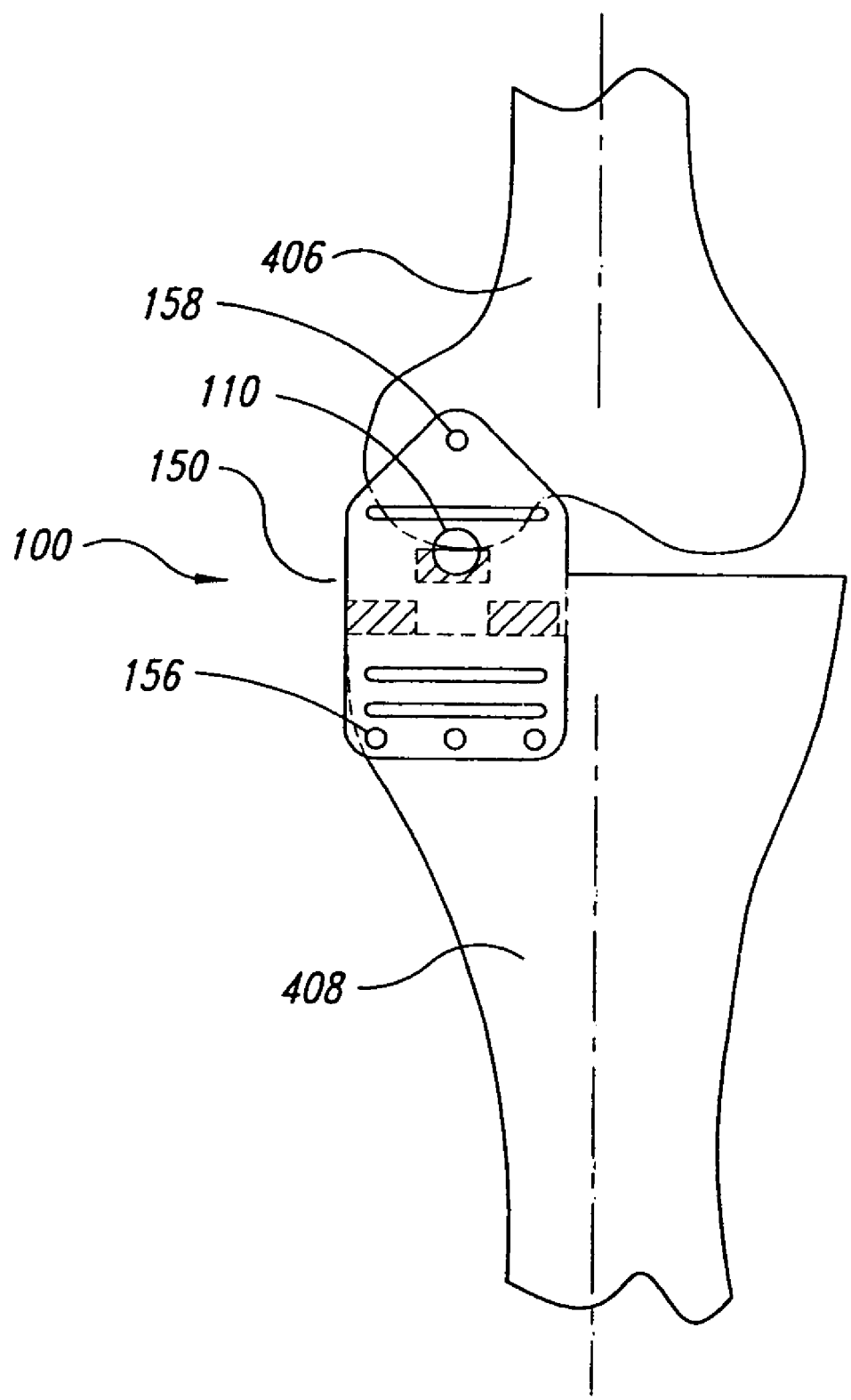
FIG. 39 is a front elevation view of the knee of FIG. 38 after a cutting guide according to one embodiment of the present invention has been mounted to the alignment device.
Figure 40:
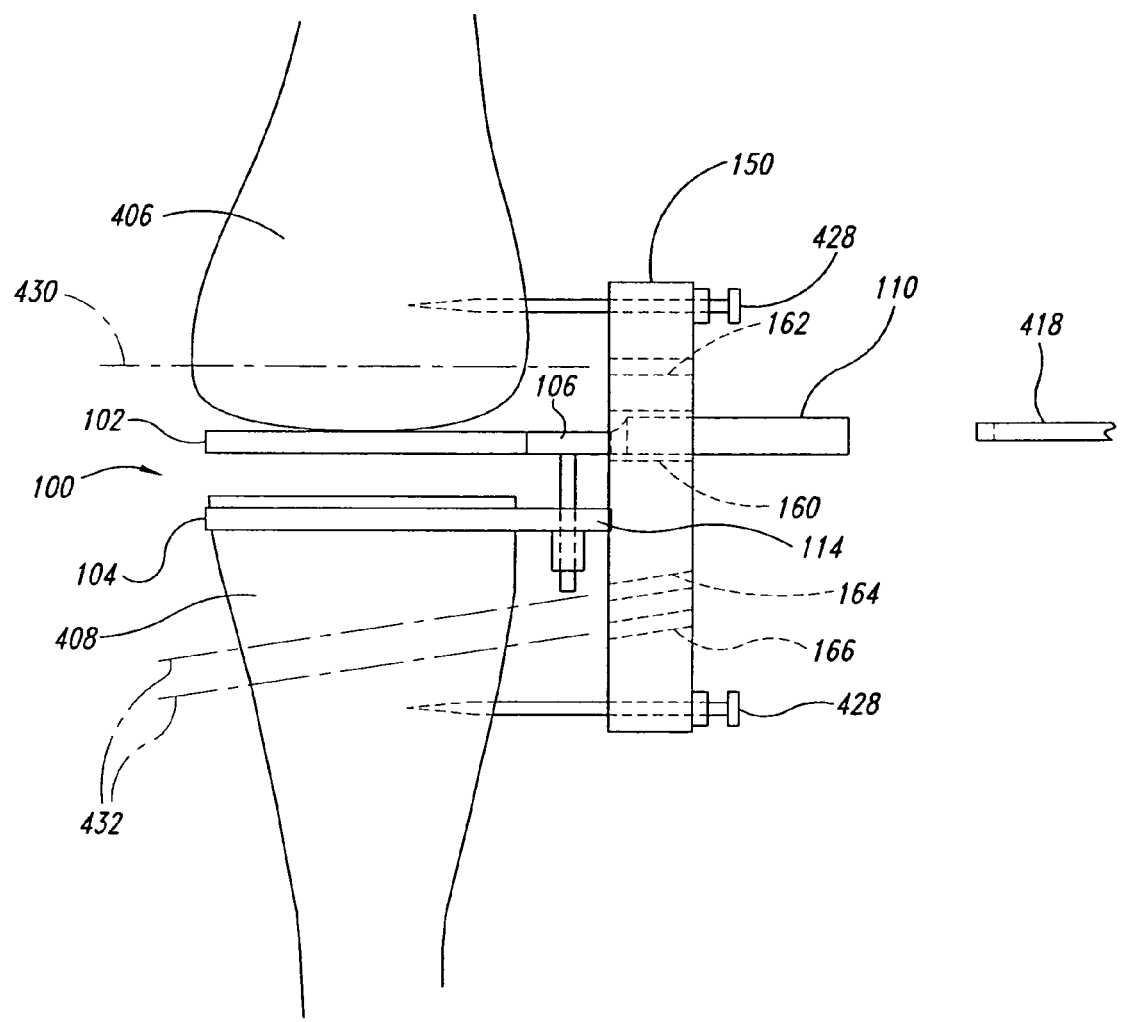
FIG. 40 is a side elevation view of the knee, alignment device and cutting guide of FIG. 39.

FIGS. 39 and 40 illustrate the next step in this particular method of the present invention. After the alignment rod and alignment block 424/426 are removed from the post 110 of the alignment device 100, the cutting guide 150 can be installed on the post. The mounting opening 160 (FIG. 16) on the cutting guide 150 is slid over the post 110 of the alignment device 100 until the cutting guide 150 contacts the central body 106 of the first member 102 and/or the base 114 of the second member 104. The practitioner can rotate the cutting guide 150 about the post 110 until the cutting guide is in the desired alignment (e.g., perpendicular to the mechanical or weight-bearing axis of the tibia), and fix the cutting guide 150 to the distal femur 406 and proximal tibia 408. Pins 428 can be inserted through the tibial pin guides 156 and femoral pin guide 158, and driven using the pin driver 340 (FIG. 31) into the proximal tibia 408 and distal femur 406, respectively. With the pins 428 driven into the bones, the cutting guide 150 is maintained in a fixed relationship with respect to both the distal femur 406 and the proximal tibia 408. The cutting guide 150 accordingly is in a fixed position to guide the practitioner when making the horizontal, femoral and tibial cuts.

As best illustrated in FIG. 40, the femoral cutting groove 162 is aligned to direct the surgical saw 418 against the distal femur 406. As discussed above in connection with FIG. 17, the horizontal femoral cut 430 is approximately 3.5 millimeters from the extreme distal end of the distal femur 406 to accommodate the femoral implant 200. The scale illustrated in portions of FIGS. 37-42 has been distorted to best illustrate the invention.

The first and second tibial cutting grooves 164/166 are aligned to guide the surgical saw 418 against the proximal tibia 408. As discussed above in connection with FIG. 17, the first tibial cutting guide 164 is located to place the horizontal tibial cut 432 eight millimeters from the extreme distal end of the distal femur 406, and the second tibial cutting guide 166 is located to position the horizontal tibial cut ten millimeters from the extreme distal end of the distal femur.

After the horizontal, tibial and femoral cuts have been completed, the pins 428 or other fasteners retaining the cutting guide 150 to the distal femur 406 and proximal tibia 408 can be removed to separate the cutting guide from the patient. The alignment device 100 can then be slid from between the distal femur 406 and the proximal tibia 408. If necessary, the surgical saw 418 can be used to complete any cuts, or to separate any remaining bone from the newly cut area. For example, the practitioner may make a vertical cut at the central edge of the horizontal, tibial or femoral cut to separate a remaining portion of bone.

At this point in the procedure, the distal femur 406 is prepared to be shaped for receiving a trial femoral implant 200. The mounting instrument 300 can be engaged at its threaded end 308 with the threaded opening 186 on the cutting/drilling guide 170. With the lower surface 176 of the cutting/drilling guide 170 urged against the surface of the distal femur created by the horizontal femoral cut, the practitioner can attach the cutting/drilling guide to the femur by driving pins or using screws through the pinholes 184. Once the cutting/drilling guide 170 has been fixed to the distal femur 406, the practitioner can rotate the handle 304 of the mounting instrument 300 to remove the mounting instrument from the cutting/drilling guide. The practitioner can use the surgical saw 418 to make the superior posterior chamfer cut through the bevel cut guide 179 and the posterior articulating surface cut through the posterior cut guide 180, and can use a surgical drill to bore the mounting holes in the distal femur using the mounting hole guides 182. These cuts and holes are configured for mounting the trial femoral implant 200, which conforms with a currently standard femoral prosthesis; these cuts and holes can vary as the shape and configuration of femoral prostheses change between manufacturers and over time. After removing the pins, the practitioner can separate the cutting/drilling guide 170 from the distal femur 406.

The tibial surface is then sized and prepared according to the guidelines for the specific prosthesis being utilized. The practitioner may then temporarily implant the trial prosthesis to confirm the alignment, stability and fit.

To mount the trial femoral implant 200 on the distal femur 406, the practitioner engages the threaded end 308 of the mounting instrument 300 with the threaded hole 216 on the prosthesis. The practitioner then prepares the prosthesis and/or distal femur 406 with adhesives or other bonding agents and urges the femoral prosthesis against the distal femur using the mounting instrument 300. It is impacted into place with standard instruments.

The practitioner can then implant the tibial prosthesis. Because the practitioner selected the desired alignment in the leg prior to making the horizontal, tibial and femoral cuts, the practitioner can implant the pre-selected tibial prosthesis knowing that the alignment in the leg is likely to be the desired alignment. The practitioner can implant the tibial prosthesis in the standard manner.

The method of the present invention has many advantages over the methods of the prior art. For example, the method of this particular embodiment of the present invention may allow the practitioner to select the desired ultimate alignment of the patient's leg prior to making the horizontal tibial and horizontal femoral cuts. As a result, the practitioner can make each of these cuts only once and obtain the proper alignment between the tibia and the femur. The cuts are assured to be parallel, which can be important for long-term survival of the implant. This method thus may eliminate the requirement that the practitioner make multiple cuts to create the proper leg alignment.

The procedure of this embodiment of the present invention may also allow the practitioner to align the leg and make the horizontal, tibial and femoral cuts all through an incision that is significantly smaller than those used in prior art procedures. As a result, the risk and recovery time may be reduced for the patient.

This method is performed without using intramedullary rods. Performing this procedure without intramedullary rods may also have benefits to the patients.

Figure 41:
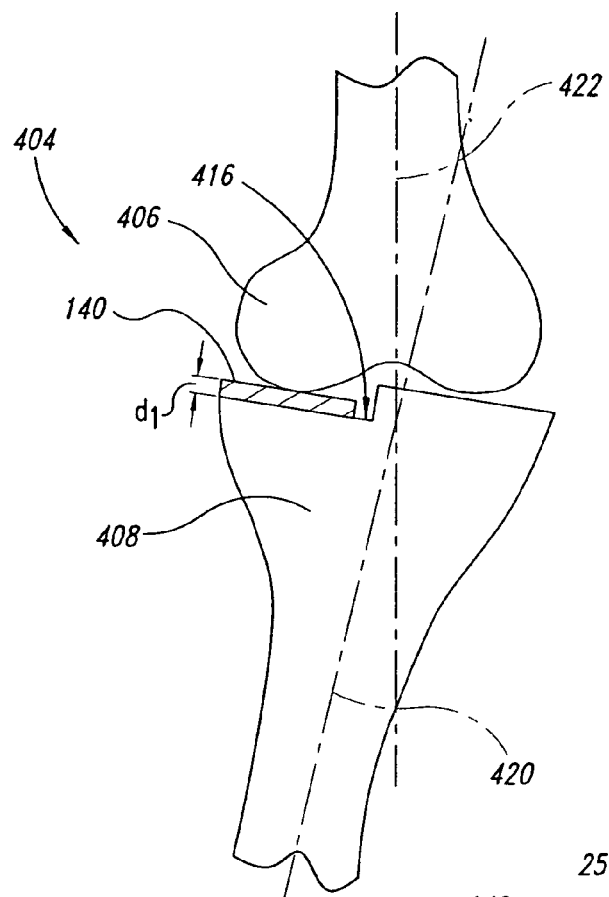
FIG. 41 is a front elevation view of a knee and first spacer according to another embodiment of the present invention.
Figure 42:
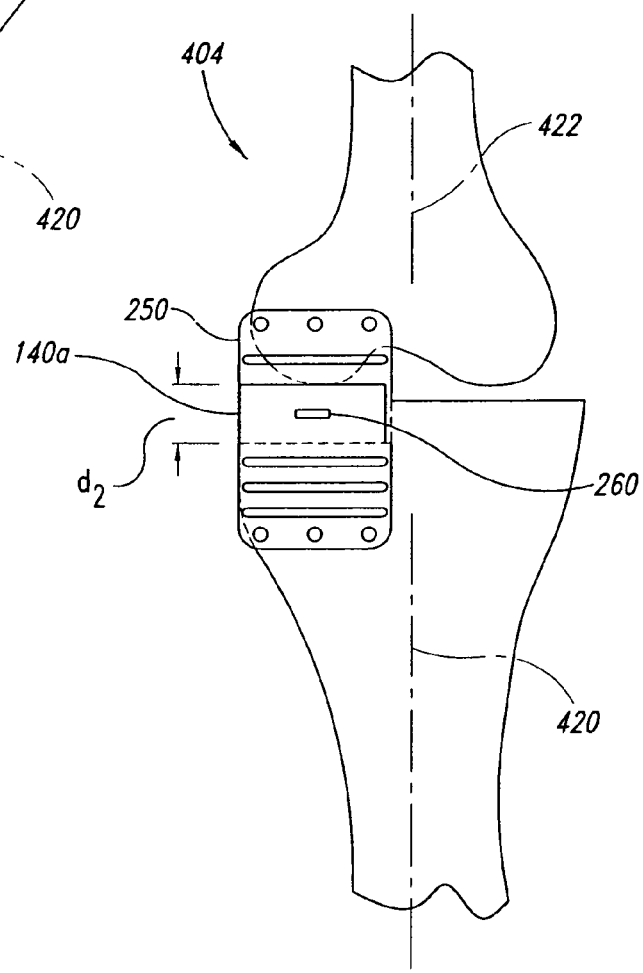
FIG. 42 is a front elevation view of the knee of FIG. 41 in which the first spacer has been replaced by a second spacer, and another cutting guide according to another embodiment of the present invention.

FIGS. 41 and 42 illustrate another method of aligning a leg 404, and for aligning horizontal, tibial and femoral cuts according to another embodiment of the present invention. In FIG. 41, the spacer 140 has been inserted between the distal femur 406 and the flat surface 416 on the proximal tibia 408. The spacer 140 illustrated in FIG. 41 is too thin to create a desired alignment in which the tibial axis 420 is collinear with the femoral axis 422. Accordingly, the practitioner may choose to replace the spacer 140 with a different spacer having a greater thickness.

FIG. 42 illustrates the leg 404 in which the spacer 140a, having an increased thickness "d2" has been inserted between the distal femur 406 and the proximal tibia 408. As illustrated in FIG. 42, the distance "d2" is appropriate to create an alignment in which the tibial axis 420 is collinear with the femoral axis 422. In this configuration, the leg 404 is aligned for the practitioner to perform the horizontal, femoral and tibial cuts.

FIG. 42 also illustrates the cutting guide 250 according to this alternate embodiment of the present invention. The rectangular mounting opening 260 has been engaged with the spacer 140a in a fixed orientation with respect to the leg 404. The cutting guide 250 can now be fixed to the distal femur 406 and proximal tibia 408, and the horizontal femoral cut 430 and horizontal tibial cut 432 (FIG. 40) can be made.

Although the methods described above have been performed on a leg where the proximal tibia has been cut prior to insertion of the alignment device or spacer, the method of the present invention can in some instances be performed without the preliminary tibial cut. In such cases the alignment device or spacer would be inserted between the distal femur and the tibial plateau, and adjusted to create the desired alignment as discussed above.

The methods of the present invention can be performed on the opposite side of the leg or on both sides of a particular leg, as the situation demands. Accordingly, it is not the inventor's desire to specify that the invention is for the medial or lateral condyle of the left or right leg, but is instead universally applicable.

FIGS. 43-46 illustrate a combined alignment device and cutting guide 500 according to still another embodiment of the present invention. In general, the combined alignment device and cutting guide 500 incorporates many of the features of the alignment device 100 and cutting guide 150 as described above in connection with prior embodiments of the present invention. The duplicative features accordingly are not discussed in this portion of the disclosure, but are assumed to be clear based on the prior disclosure.

Figure 43:
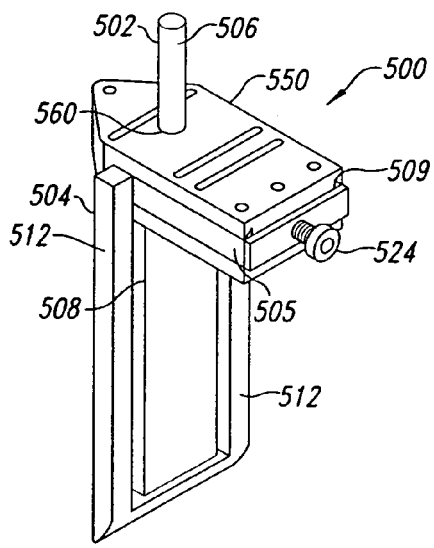
FIG. 43 is an isometric view of a combined alignment device and cutting guide according to still another embodiment of the present invention.
Figure 44:
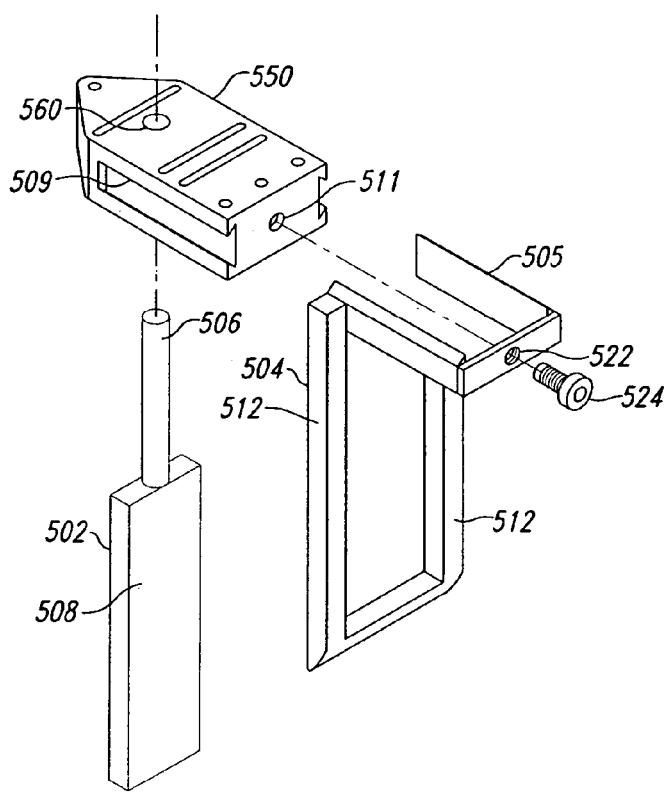
FIG. 44 is an exploded isometric view of the combined alignment device and cutting guide of FIG. 43.

FIGS. 43 and 44 best illustrate the elements and features of the combined alignment device and cutting guide 500 of this particular embodiment of the present invention. The combined alignment device and cutting guide 500 incorporates a first member 502, a second member 504 and a cutting guide 550. A shaft 506 on the first member 502 engages a mounting opening 560 on the cutting guide 550. A prong 508 on the first member 502 projects in a downward direction as illustrated in FIG. 43 from the cutting guide 550. A pair of opposing rails 505 on the second member 504 are engaged with a complementary pair of grooves 509 in the cutting guide 550. In the configuration illustrated in FIG. 43, the rails 505 of the second member 504 have been slid into the grooves 509 in the cutting guide 550 to a point in which a pair of legs 512 on the second member are generally coplanar with the prong 508 on the first member 502. A screw 524 is engaged with a hole 522 in the second member 504 and contacts a depression 511 in the cutting guide 550. Rotation of the screw in the clockwise direction within the threaded hole 522 causes the screw to move through the second member 504 and into the depression 511. Once the screw 524 contacts the depression 511, continued rotation of the screw in the clockwise direction causes the second member 504 to move away from the cutting guide 550. As a result, rotation of the screw 524 moves the legs 512 apart from the prong 508 in a similar manner to manipulation of the alignment device 100 discussed above.

Figure 45:
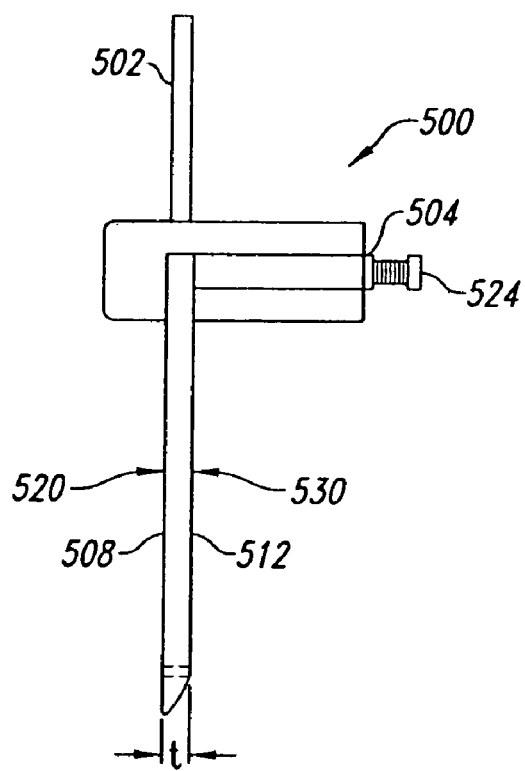
FIG. 45 is a side elevation view of the combined alignment device and cutting guide of FIG. 43, in a first position.
Figure 46:
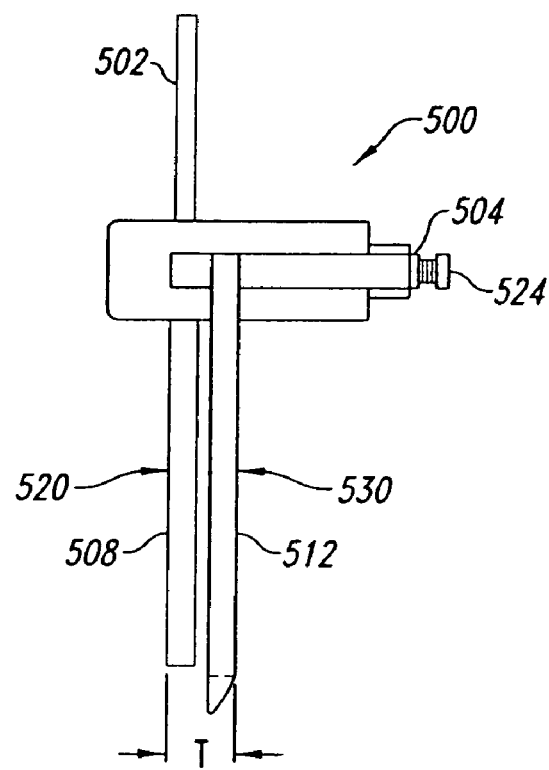
FIG. 46 is a side elevation view of the combined alignment device and cutting guide of FIG. 43, in a second position.

FIGS. 45 and 46 illustrate the combined alignment device and cutting guide 500 in two configurations. In FIG. 45, the screw 524 has been threaded out of the second member 504 to allow the second member to align with the first member 502. The prong 508 consequently is positioned coplanar with the legs 512. This alignment results in a minimum thickness "t" between a lower surface 520 and a top surface 530, similar to that discussed above in connection with alignment device 100.

In FIG. 46, the screw 524 has been threaded into the second member 504 to move the second member apart from the first member 502. As a result, the lower surface 520 is spaced apart from the top surface 530 by an increased distance "T". This increased distance "T" can be used by the practitioner as discussed above to manipulate the spacing and alignment of the patient's leg. Once the leg is in the desired alignment, the cutting guide 550 can be fixed to the patient's leg using pins or screws, and the physician can make the horizontal, tibial and femoral cuts as generally discussed above.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A prosthetic implant for a knee replacement procedure that uses an externally threaded instrument to urge the implant against a distal femur during the procedure, the implant comprising:

a body having an inner surface configured to mate with the distal femur, an outer surface configured for sliding engagement with a tibial implant, and an opening extending from the outer surface at least partially toward the inner surface, wherein the opening in the body of the implant includes internal threads initiating proximate to the outer surface and extending toward the inner surface to releasably, fixedly engage a complementary, threaded portion of the instrument.

2. The implant of claim 1 wherein the opening is centrally located with respect to the outer surface.

3. The implant of claim 1 wherein the opening extends entirely through the body of the implant.

4. The implant of claim 1 wherein the inner surface of the implant further comprises at least one protuberance for engagement with a complementary mounting hole in the distal femur, and wherein a longitudinal axis defined by the opening in the body of the implant is generally aligned with the at least one protuberance.

5. The implant of claim 1 wherein the inner surface of the implant further comprises a pair of protuberances for engagement with a complementary pair of mounting holes in the distal femur, and wherein a longitudinal axis defined by the opening in the body is at least substantially parallel with and positioned between the protuberances.

6. The implant of claim 1 wherein the inner surface is configured to mate with the femur after a portion of the femur has been removed.

7. An implant for use in a knee replacement procedure that uses an externally threaded instrument to urge the implant against a distal femur during the procedure, the implant comprising:
a tibial prosthesis configured to be attached to a distal end of a tibia; and
a femoral prosthesis having an inner surface configured to mate with at least a portion of the distal femur, an outer surface configured for sliding engagement with the tibial prosthesis, and an opening extending from the outer surface at least partially toward the inner surface, wherein the opening in the body of the implant includes internal threads engageable from outside the outer surface and extending toward the inner surface to releasably, fixedly engage a complementary, threaded portion of the instrument.

8. The implant of claim 7 wherein the opening is centrally located with respect to the outer surface.

9. The implant of claim 7 wherein the opening extends entirely through the body of the implant.

10. The implant of claim 7 wherein the inner surface of the implant further comprises at least one protuberance for engagement with a complementary mounting hole in the distal femur, and wherein a longitudinal axis defined by the opening in the body of the implant is generally aligned with the at least one protuberance.

11. The implant of claim 7 wherein the inner surface of the implant further comprises a pair of protuberances for engagement with a complementary pair of mounting holes in the distal femur, and wherein a longitudinal axis defined by the opening in the body is at least substantially parallel with and positioned between the protuberances.

12. A prosthetic implant for a knee replacement procedure that uses an instrument to urge the implant against a distal femur during the procedure, the implant comprising:
a body having an inner surface and an outer surface, the inner surface comprised of at least three planar surfaces configured to mate with the distal femur, the outer surface configured for sliding engagement with a tibial implant, and an opening including internal threads and extending entirely through the body of the implant from the outer surface to the inner surface, the opening configured to releasably, fixedly engage a complementary portion of the instrument.

13. The implant of claim 12 wherein the opening intersects two of the planar surfaces of the inner surface.

14. The implant of claim 12 wherein the inner surface of the implant includes at least one protuberance configured to engage a complementary mounting hole in the distal femur.

15. The implant of claim 14, further comprising:
a longitudinal axis defined by the opening in the body, wherein the longitudinal axis is generally aligned with the at least one protuberance.

16. The implant of claim 12, further comprising:
a first protuberance extending from one of the planar surfaces of the inner surface, the first protuberance configured to engage a first complementary mounting hole in the distal femur; and
a second protuberance extending from another of the planar surfaces of the inner surface, the second protuberance configured to engage a second complementary mounting hole in the distal femur, wherein the first protuberance and the second protuberance are substantially parallel.

17. The implant of claim 16, further comprising:
a longitudinal axis defined by the opening in the body that is substantially parallel with and positioned between the first protuberance and the second protuberance.

18. A prosthetic implant for a knee replacement procedure that uses an instrument to urge the implant against a distal femur during the procedure, the implant comprising:
a body having an inner surface and an outer surface, the inner surface comprised of at least three planar surfaces configured to mate with the distal femur, the outer surface configured for sliding engagement with a tibial implant, and an opening extending entirely through the body of the implant from the outer surface to the inner surface, the opening configured to releasably, fixedly engage a complementary portion of the instrument, wherein the opening intersects two of the planar surfaces of the inner surface.

19. A prosthetic implant for a knee replacement procedure that uses an instrument to urge the implant against a distal femur during the procedure, the implant comprising:
a body having an inner surface and an outer surface, the inner surface comprised of at least three planar surfaces configured to mate with the distal femur, the outer surface configured for sliding engagement with a tibial implant, and an opening intersecting two of the planar surfaces of the inner surface and extending entirely through the body of the implant from the outer surface to the inner surface, the opening configured to releasably, fixedly engage a complementary portion of the instrument.

* * * * *